United States Patent
Lorenz

(10) Patent No.: US 7,299,699 B2
(45) Date of Patent: Nov. 27, 2007

(54) COMPOSITE SYSTEM, METHOD FOR ITS MANUFACTURE, AND MEASUREMENT PICKUP USING SUCH A COMPOSITE SYSTEM

(75) Inventor: Rainer Lorenz, Lörrach (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 11/242,803

(22) Filed: Oct. 5, 2005

(65) Prior Publication Data

US 2006/0083941 A1 Apr. 20, 2006

Related U.S. Application Data

(60) Provisional application No. 60/617,642, filed on Oct. 13, 2004.

(30) Foreign Application Priority Data

Oct. 5, 2004 (DE) ...................... 10 2004 048 765

(51) Int. Cl.
*G01H 11/00* (2006.01)
*G01F 15/18* (2006.01)

(52) U.S. Cl. .................................... 73/649; 73/861.355

(58) Field of Classification Search ................. 73/649, 73/866.355, 861.356, 861.357
See application file for complete search history.

(56) References Cited

U.S. PATENT DOCUMENTS 4,090,382 A 5/1978 Schott
4,680,838 A 7/1987 Astl 6,598,281 B2 7/2003 Cook et al.

FOREIGN PATENT DOCUMENTS

DE 38 12583 A1 10/1989

(Continued)

*Primary Examiner*—Helen Kwok
(74) *Attorney, Agent, or Firm*—Bacon & Thomas, PLLC

(57) ABSTRACT

A composite system includes a first component, for instance of metal, and a second component extending at least partly through the first component along an imaginary longitudinal axis of the composite system. The second component contacts, with an at least partially curved, especially cylindrical, outer surface, an inner surface of the first component flushly such that the first component at least sectionally, at least partly, grips around the second component. Joining surfaces of the composite system, which are formed by the mutually contacting surfaces of the two components, are formed in such a manner that the two components exhibit contour portions in the area of these joining surfaces embodied as self-closing, peripheral surfaces. The contour portions fit at least partly into one another, to form a mechanical interference locking effective, at least in part, likewise in the direction of the longitudinal axis. Additionally, the second component, with its outer surface, contacts the inner surface of the first component flushly, such that the two components are mechanically tightly connected together also by means of a frictional locking effective at least partly in the direction of the longitudinal axis. Alternatively, or in supplementation thereof, at least one of the components is subjected at least partly to lastingly elastic, especially mixed plastic-elastic, deformations. The composite system is distinguished by a high pull-out strength, even in the presence of repeatedly arising vibrations in one of the components and is, therefore, especially suited also for use in a vibration-type measurement pickup.

59 Claims, 6 Drawing Sheets

FOREIGN PATENT DOCUMENTS

| | | |
|---|---|---|
| DE | 3812583 | 10/1989 |
| DE | 43 27 461 A1 | 10/1994 |
| DE | 4327461 | 10/1994 |
| DE | 199 36 008 A1 | 3/2001 |
| DE | 101 15 141 A1 | 10/2002 |
| DE | 10115141 | 10/2002 |
| EP | 0 685 712 B1 | 5/2000 |
| EP | 0 866 317 B1 | 1/2001 |
| EP | 1 113 248 A3 | 7/2001 |
| EP | 0 702 213 B1 | 9/2003 |
| GB | 2 261 837 A | 6/1993 |
| JP | 5 814 4714 A | 8/1983 |
| JP | 5 910 9818 A | 6/1984 |
| JP | 6 126 9021 A | 11/1986 |
| WO | WO 87/01428 | 3/1987 |
| WO | WO 03/ 021202 A1 | 3/2003 |
| WO | WO 03/048693 A1 | 6/2003 |

2,77 mm

COMPOSITE SYSTEM, METHOD FOR ITS MANUFACTURE, AND MEASUREMENT PICKUP USING SUCH A COMPOSITE SYSTEM

FIELD OF THE INVENTION

The application claims the benefit of provisional application No. 60/617,642 filed on Oct. 13, 2004.

The invention relates to a composite system involving a first component, especially a first component of metal, and a second component, especially a second component likewise of metal, joined with the first component, especially in the context of a vibration-type measurement pickup having at least one measuring tube which vibrates in operation. Additionally, the invention relates to a method for manufacturing such a composite system, especially for application in a measurement pickup of vibration-type.

BACKGROUND OF THE INVENTION

In the technology of industrial measurements and automation, inline measuring devices having a vibration-type measuring pickup are used for high-accuracy registering of measured process variables, especially flow-dynamic and/or rheological, measured variables, of media flowing in conduits, especially pipelines. Such measuring devices typically include at least one measuring tube communicating with the medium-conveying pipeline and vibrating during operation. Construction, functioning and examples of use of such measurement pickups of vibration-type are described in detail, for example, in U.S. Pat. No.-A 4,127,028, U.S. Pat. No.-A 4,524,610, U.S. Pat. No.-A 4,768,384, U.S. Pat. No.-A 4,793,191, U.S. Pat. No.-A 4,823,614, U.S. Pat. No.-A 5,253,533, U.S. Pat. No.-A 5,610,342, U.S. Pat. No.-A 6,006,609, U.S. Pat. No.-A 6,047,457, U.S. Pat. No.-B 6,168,069, U.S. Pat. No.-B 6,314,820, U.S. Pat. No.-B 6,352,196, U.S. Pat. No.-B 6,397,685, U.S. Pat. No.-B 6,450,042, U.S. Pat. No.-B 6,487,917, U.S. Pat. No.-B 6,516,674, U.S. Pat. No.-B 6,519,828, U.S. Pat. No.-B 6,523,421, U.S. Pat. No.-B 6,598,281, U.S. Pat. No.-B 6,666,098, U.S. Pat. No.-B 6,698,644, U.S. Pat. No.-B 6,711,958, U.S. Pat. No.-A 6,769,163, WO-A 03/048693, or the assignee's not pre-published German Application DE 10354373.2.

Vibration-type measurement pickups serve, as is known, to produce, in conjunction with a measuring device electronics connected thereto, reaction forces in the medium at the moment conveyed in the at least one measuring tube. These reaction forces correspond with the process variables to be measured and include e.g. Coriolis forces corresponding with a mass flow rate, inertial forces corresponding with a density, or frictional forces corresponding with a viscosity, etc. Measurement signals are then derived from these forces, appropriately corresponding with the measured process variables, for example the particular mass flow rate, viscosity and/or density of the medium. The at least one measuring tube of the measurement pickup is usually medium-tight, especially pressure-tight, for this purpose and is most often inserted permanently into the course of the pipeline conveying the medium, for instance by means of flange connections. For the oscillatable holding of the at least one measuring tube, a tubular or frame-shaped support element is provided. The support element, for example of steel, is usually made to be very resistant to bending, as compared to the measuring tube, and is mechanically coupled to the particular measuring tube, for example directly affixed thereto, at the inlet and outlet ends. The support element can, as is usual for such measurement pickups and also clearly evident from the aforementioned state of the art, be completed to form the already mentioned measurement pickup housing by means of appropriately, externally applied coverings, such as e.g. tube-covering caps or laterally applied sheets, or it can even itself be constructed as a measurement pickup housing.

For driving the at least one measuring tube, measurement pickups of the described kind additionally include an exciter arrangement electrically connected with the particular measuring device electronics. The exciter arrangement includes an oscillation exciter, especially an electrodynamic or electromagnetic oscillation exciter, acting mechanically on the measuring tube. In operation, the exciter arrangement is driven by the measuring device electronics by means of appropriate exciter signals in suitable manner such that the measuring tube at least temporarily executes vibrations, especially bending oscillations and/or torsional oscillations. Additionally, a sensor arrangement is provided for producing oscillation measurement signals and having, at least in the case of application of the measuring pickup as a Coriolis mass flow measurement pickup, at least two mutually separated sensor elements reacting to inlet and/or outlet vibrations of the measuring tube.

Besides the possibility of simultaneously measuring a plurality of such process variables, especially mass flow rate, density and/or viscosity, by means of one and the same measuring device, another essential advantage of inline measuring devices having measurement pickups of vibration-type, is that they exhibit, within specified operational limits, a very high measurement accuracy coupled with relatively low sensitivity to disturbances. Moreover, such a measuring device can be used for practically every flowable medium and applied in a multitude of the most varied application areas of the technology of measurements and automation.

In the case of inline measuring devices of the described kind applied as Coriolis mass flow meters, the particular measuring device electronics determines, among other things, a phase difference between the two oscillation measurement signals delivered by the two sensor elements and the measurement electronics issues at its output a measured value signal derived therefrom, which represents a measured value corresponding to the time behavior of the mass flow rate. If, as usual in the case of such inline measuring devices, also the density of the medium is to be measured, then the measuring device electronics additionally determines for such purpose an instantaneous oscillation frequency of the measuring tube on the basis of the oscillation measurement signals. Moreover, also, for example, the viscosity of the medium can be measured on the basis of the power required for maintaining the oscillations of the measuring tube, especially a corresponding exciter current for the exciter arrangement.

For operating the measurement pickup, especially for the further processing or evaluation of the at least one measurement signal, the measurement pickup is, as already indicated, connected with a corresponding measuring device electronics. In the technology of industrial measurements and automation, this measuring device electronics is often connected for this purpose via an associated data transmission system, e.g. via a digital data bus, with other measuring devices and/or with a remote, central computer, to which it sends the measured-value signals. Serving as data transmission systems in this case are often bus systems, especially serial bus systems, such as e.g. PROFIBUS-PA, FOUNDA- TION FIELDBUS, and the corresponding transmission protocols. By means of the central computer, the transmitted measured-value signals can be processed further and visualized as corresponding measurement results e.g. on monitors and/or converted into control signals for appropriate adjustment means, such as e.g. magnetic valves, electromotors of pumps, etc. For accommodating the measuring device electronics, such inline measuring devices further include an electronics housing, which, as e.g. proposed in WO-A 00/36379, can be located remotely from the measurement pickup and connected therewith simply over a flexible line, or which, as shown e.g. also in EP-A 1 296 128 or WO-A 02/099363, is arranged directly on the measurement pickup, especially on top of a measurement pickup housing accommodating the measurement pickup.

In the case of measurement pickups of the described kind, essentially two kinds of tube shapes have become established on the market, namely, on the one hand, essentially straight measuring tubes, and, on the other hand, measuring tubes essentially curving in a tube plane, among which those having essentially S-, U- or V-shape are most frequently used. Especially in the case of Coriolis mass flow measurement pickups serving for the measurement of mass flow rates, in the case of both kinds of tube forms, for reasons of symmetry, mostly two measuring tubes are used, which, at rest, extend essentially parallel to one another and most often are flowed through by medium also in parallel. In this connection, reference can be made, by way of example, to U.S. Pat. No.-A 4,127,028, U.S. Pat. No.-A 4,768,384, U.S. Pat. No.-A 4,793,191, U.S. Pat. No.-A 5,610,342, U.S. Pat. No.-A 5,796,011 or U.S. Pat. No.-B 6,450,042.

Besides measurement pickups with such double measuring tube arrangements, however, also measurement pickups having a single, straight or curved, measuring tube have been available for a long time on the market. Such measurement pickups of vibration-type with a single measuring tube are described e.g. in U.S. Pat. No.-A 4,524,610, U.S. Pat. No.-A 4,823,614, U.S. Pat. No.-A 5,253,533, U.S. Pat. No.-A 6,006,609, U.S. Pat. No.-B 6,314,820, U.S. Pat. No.-B 6,397,685, U.S. Pat. No.-B 6,487,917, U.S. Pat. No.-B 6,516,674, U.S. Pat. No.-B 6,666,098, U.S. Pat. No.-B 6,698,644, U.S. Pat. No.-B 6,711,958, WO-A 03/048693, or the assignee's mentioned application DE 10354373.2. Each of the measurement pickups shown therein includes, among other things, a measuring tube having an inlet end and an outlet end and vibrating, at least at times, especially a measuring tube of steel, titanium, tantalum or zirconium or corresponding alloys, for the conveying of the medium to be measured, wherein the measuring tube communicates with a connected pipeline via a first tube segment opening into the inlet end and via a second tube segment opening into the outlet end for enabling the flow-through of the medium and wherein the measuring tube executes, during operation, mechanical oscillations about an oscillation axis imaginarily connecting the two tube segments, as well as including a mostly very bending-stiff, tubular or frame-shaped, support element, for example of steel, for the oscillatable holding of the measuring tube, which is affixed to the first tube segment by means of a first transition piece and to the second tube segment by means of a second transition piece.

For the above-described case, that the measurement pickup being utilized is one involving a single measuring tube, counter oscillator means is/are additionally provided in the measurement pickup, suspended oscillatably in the measurement pickup housing and affixed to the measuring tube, in order, apart from the holding of the oscillation exciter and the sensor elements, to decouple the vibrating measuring tube from the connected pipeline as regards oscillation. The counter oscillator, which is usually made of a cost-favorable steel, can, in such case, be embodied e.g. as a tubular compensation cylinder or box-shaped support frame arranged coaxially with the measuring tube. To the referenced assembly of features of the separate, above-described, measurement pickups is still to be added that a straight measuring tube, or straight measuring tubes, is/are mostly made of pure titanium, a titanium alloy with high titanium content, pure zirconium, or a zirconium alloy with high zirconium content, since, compared with measuring tubes of stainless steel, which is, per se, likewise possible in the case of straight measuring tubes, usually shorter constructed lengths result, and that a curved measuring tube, or measuring tubes, is/are preferably made of stainless steel, although titanium or zirconium, or their alloys are also possible as material for the measuring tubes. Moreover, however, also the use of, for example, tantalum or corresponding tantalum alloys is usual as measuring tube material.

As can be derived from the above explanations without difficulty, practically each of the measurement pickups evidenced in the above-referenced state of the art has at least one composite system, especially a bimetallic composite system, which includes a first component—for example, the first or the second end piece—and a second component—for example, the measuring tube—extending at least partly through the first component along an imaginary longitudinal axis of the composite system, wherein usually the second component contacts an inner surface of the first component flushly with an outer, cylindrical surface, the inner surface being formed by the inner wall of a bore extending within the first component. Equally, however, there are also measurement pickups using a double measuring tube arrangement, such as described especially also in U.S. Pat. No.-A 5,610,342, constructed of a plurality of such, especially bimetallic, composite systems. Besides the composite system formed by measuring system and end piece, other examples of such, especially bimetallic, composite systems are especially also the connection of measuring tube and flange, or the connection of flange and measurement pickup housing; compare, in such connection, also U.S. Pat. No.-B 6,168,069, U.S. Pat. No.-B 6,352,196, U.S. Pat. No.-B 6,698,644. By way of example and as also described in U.S. Pat. No.-A 6,047,457, a circular, washer-shaped, metal body can be affixed on the measuring tube halfway between the end pieces, to serve as part of the exciter arrangement or to interact with such.

Very high requirements are placed on vibration-type measurement pickups used in industrial measuring and automation technology as regards accuracy of measurement, which usually lies in the range of about 0.1% of the measured value and/or 0.01% of maximum reading. For this, especially a very high stability of the zero point is required, as well as also a very high robustness of the delivered measurement signals, especially also in the case where environmental, clamping and/or operating conditions are significantly changing. As already extensively discussed in the mentioned U.S. Pat. No.-A 5,610,342, U.S. Pat. No. 6,047,457, U.S. Pat. No.-A 6,168,069, U.S. Pat. No.-B 6,519,828, U.S. Pat. No.-B 6,598,281, U.S. Pat. No.-A 6,698,644, U.S. Pat. No.-B 6,769,163, WO-A 03/048693, or the mentioned application DE10354373.2 of the present assignee, in such case, considerable importance is given also to the mechanical strength, especially fatigue strength, with which the separate components of the aforementioned composite systems formed in the measurement pickup are affixed to one another. Already the slightest departure of the strength of the aforementioned composite systems from the situation existing during calibration can result in significant, no longer manageable, fluctuations of the zero point and, consequently, in practically unusable measurement signals. Usually, such zero-point errors attributable to loss-of-strength phenomena in the composite systems can only be removed by complicated repair measures performed remote from the pipeline or only by installation of a new, inline, measuring device. Having a special influence on the stability of the zero-point and/or the availability of the measurement pickup is, in such case, as, in fact, also already discussed extensively in U.S. Pat. No.-A 5,610,342, U.S. Pat. No.-A 6,047,457, U.S. Pat. No.-B 6,168,069, U.S. Pat. No.-A 6,598,281, U.S. Pat. No.-B 6,634,241 or also WO-A 03/048693, the manner in which the measuring tube is secured within the outer support element and relative to the possibly present counter oscillator.

Traditionally, the components of such composite systems are at least partly bonded together by solder, braze and/or weld connections. Thus, it is, for example, already described in U.S. Pat. No.-A 4,823,614, that each end of the one measuring tube is inserted into a respective bore of an inlet or outlet endpiece and affixed therein by welding, soldering or brazing front and back; compare the material beads visible in some of the figures. The endpieces are then, in turn, affixed in the outer support element. Further examples of such composite systems with bonded connections are shown in, among others, also in U.S. Pat. No. 6,168,069, U.S. Pat. No.-B 6,352,196, U.S. Pat. No.-B 6,519,828, U.S. Pat. No.-B 6,523,421, U.S. Pat. No.-B 6,598,281, U.S. Pat. No.-B 6,698,644 or U.S. Pat. No.-B 6,769,163.

As described in U.S. Pat. No.-A 5,610,342, the heat needed for the mentioned welding, soldering or brazing leaves behind, following cooling, residual stresses at the locations of the joints between the measuring tubes and the end pieces which can lead to stress corrosion cracking, which can, to a greater or lesser degree, weaken the joints and/or the material of the measuring tube. As a further problem with such bonded, weld, solder or braze connections, also material-wearing, oscillatory rubbing in the area of the joints is mentioned in U.S. Pat. No.-B 6,519,828 or U.S. Pat. No.-B 6,598,281. Moreover, as can perceived from the basis of U.S. Pat. No.-A 6,047,457, U.S. Pat. No.-B 6,168,069, U.S. Pat. No.-B 6,352,196, U.S. Pat. No.-B 6,598,281, U.S. Pat. No.-B 6,634,241, U.S. Pat. No.-B 6,523,421 or U.S. Pat. No.-B 6,698,644, especially in the case of bimetal composite systems, thus those systems where the first component and the second component are different metals, for example steel and titanium, problems can arise as regards the long-term strength, for instance fatigue strength, of the solder connections, which problems can be attributed, among other things, to insufficient wetting and/or radially directed, alternating, mechanical loading of the joints. As a result of this, often a lessening of the nominal pull-out strength of the composite system, measured in the direction of its longitudinal axis, is to be noted.

For improving the long-term strength of such composite systems, for example formed of a measuring tube of a Coriolis mass flow rate measurement pickup and a metal body pushed onto the measuring tube, and then affixed thereon, the already-mentioned U.S. Pat. No.-A 5,610,342, as well as also WO-A 03/048693, disclose a securement method for measuring tubes in end pieces, in which each end of the measuring tube is inserted into a corresponding bore of an inlet or outlet, end piece and pressed, by means of a rolling tool placed in the end, against the inner wall of the bore, especially without addition of heat, whereby a high-strength, friction connection is formed between the first and second components. A rolling tool suited for this method is described, for instance, also in U.S. Pat. No.-A 4,090,382, in the context of a method for manufacturing boilers or heat exchangers.

A further possibility for manufacturing such composite systems formed by means of high-strength, friction connections includes, as e.g. proposed also in U.S. Pat. No.-A 6,047,457, that the first component, after having been pushed, or inserted, onto the second component, is compressed by means of an externally applied pressing tool and, in the process, deformed mixed plastically-elastically below a recrystallization temperature of the component-material, especially at room temperature. The deformation forces used therefor are, in such case, always developed such that the second component essentially does not experience any cross sectional tapering and/or narrowing, so that an initial inner diameter of the second component remains essentially unchanged throughout, following the production of the composite system. An apparatus appropriately suitable for the pressing is disclosed, for example, in U.S. Pat. No.-A 3,745,633. Alternatively to the plastic-elastic pressing, such a composite system formed by means of frictional locking can, for example, also be manufactured by processing wherein the first component, as also shown in U.S. Pat. No.-B 6,598,281 or U.S. Pat. No.-B 6,519,828, is thermally shrunk onto the second component or clamped to the second component with the interposing of elastically deformable clamping elements.

Taking the subject further, U.S. Pat. No.-B 6,598,281 or U.S. Pat. No.-B 6,519,828 indicate that, with press connections holding purely by friction, a possible deterioration of the composite systems can not always be avoided with certainty, due to oscillatory rubbing. Beyond this, such oscillatory rubbing can bring about the corrosion of the materials of the composite system in the area of the mutually contacting surfaces. Furthermore, as can be perceived from WO-A 03/048693, the usually differing expansion characteristics of the components of the above-described composite systems, for example thus the above-mentioned end pieces and the tubular segments of the measuring tube clamped therein, can lead to the clamping forces exerted by the first component on the second component falling below a critical value in the face of temperature fluctuations, especially in the case of possible temperature shocks, such as can e.g. arise during regularly performed cleaning measures with extremely hot washing liquids. This can, in turn, mean that the first component and the second component lose, at locations, the mechanical contact brought about by the rolling, pressing or shrinking, due to thermally related expansions, so that the composite system can be weakened to an unallowable degree. As a result, the pull-out strength of the composite system can sink, so that the desired high zero-point stability of the measurement pickup can also not, without more, be assured with such press-joined assemblies.

For overcoming the deficiency in composite systems of the described kind caused by oscillatory rubbing between the components, it is proposed in U.S. Pat. No.-B 6,598,281 or U.S. Pat. No.-B 6,519,828 to additionally weld the associated components together, following production of the press-joined assembly, especially with the use of a filler material serving as an interposed layer. However, this can possibly bring up again the above-mentioned problems associated with welded connections. In contrast, a composite system is proposed in WO-A 03/048693, which obtains an increased twist resistance by forming a groove in the inner wall of the first component extending in the direction of the longitudinal axis of the composite system. With the formation of an interlocking connection effective in a circumferential direction, this can effectively prevent a twisting of the first component relative to the second component. However, even this composite system can experience a lessening of its nominal pull-out resistance, be it due to oscillatory rubbing and/or thermally-related expansion, especially in the case of use in a measurement pickup with a measuring tube executing, at least at times, bending oscillations.

SUMMARY OF THE INVENTION

In view of the above-described disadvantages associated with the composite systems conventionally used in vibration-type measurement pickups, it is an object of the invention to improve composite systems, especially bi-metal composite systems, suited for use in vibration-type measurement pickups, such that their nominal pull-out strength can be increased without significant extra effort as regards manufacturing and/or design, especially also accompanied by retention of the advantages already achieved by the elastic, and/or mixed plastic-elastic, deformation of its components. Beyond this, it is also an object of the invention to increase the longterm strength of such composite systems, especially also despite the repeated occurrence of fluctuations of the environmental and/or medium temperature and the deformations of the components subjected to such temperature fluctuations.

To achieve these objects, the invention resides in an, especially bi-metal, composite system and/or a composite system suited for use in a measurement pickup of vibration-type. The composite system includes an, especially metal, first component and an, especially metal, second component extending at least partly through the first component along an imaginary longitudinal axis of the composite system. The second component flushly contacting an inner surface of the first component with an at least partially curved, especially cylindrically shaped, outer surface, such that the first component at least sectionally, at least partly, grips around the second component. In the composite system, the joining, especially frictionally interlocking, surfaces of the composite system formed by the mutually contacting surfaces of the two components are formed such that the two components have contour portions in the area of these joining surfaces, especially joining surfaces in the form of self-closing, peripheral surfaces, which contour portions at least partially fit into one another to provide mechanical interference locking likewise in the direction of the longitudinal axis.

Additionally, the invention resides in a vibration-type measurement pickup, especially a Coriolis mass flow rate measurement pickup, for an inline measuring device serving to measure a medium flowing in a line, which measurement pickup has at least one such composite system.

Moreover, the invention resides in a method for the manufacture of a composite system, especially one suited for application in a vibration-type measurement pickup, wherein the composite system includes a first component having an inner surface, which is formed by an inner wall of a bore extending at least into a portion of the first component, and a second component having an, especially at least sectionally cylindrical, outer wall, which forms the outer, especially cylindrical, surface of the second component. The method includes, in such case, the steps of assembling the first component with the second component in a manner such that the second component extends at least partially through the bore formed in the first component in the direction of a longitudinal axis of the composite system, as well as forming joining surfaces of the composite system connecting the first and second components together. For the forming of the joining surfaces of the composite system, deformation forces are caused to act on at least one of the two components in a manner such that least one of the two components is deformed at least partially elastically, especially mixed elastically-plastically. The inner surface of the first component and the outer surface of the second component are, in such case, additionally so formed and the deformation forces acting on the two components are so developed, that a first joining surface of the composite system formed by the inner surface of the first component, especially in the form of a self-closing, peripheral surface and a second joining surface of the composite system formed by the outer surface of the second component, especially in the form of a self-closing, peripheral surface, contact one another lastingly on the basis of mechanical interference locking effective at least in part in the direction of the longitudinal axis.

In a first embodiment of the composite system of the invention, the second component contacts with its outer surface the inner surface of the first component flushly, such that the two components are connected mechanically tightly together, partly also accompanied by formation of a frictional interlocking effective in the direction of the longitudinal axis, especially also in a peripheral direction of the outer surface of the second component, especially achieved by cold deformation of at least one of the two components and/or acting in the region of the mechanical interference interlocking.

In a second embodiment of the composite system of the invention, the frictional interlocking is formed at least partly by plastic, especially mixed elastic-plastic, deformation of at least one of the two components at a working temperature lying below a recrystallization temperature of the material.

In a third embodiment of the composite system of the invention, the frictional interlocking is formed by at least partly plastic, especially mixed elastic-plastic, deformation of the at least one component at a working temperature held at least at times in a temperature range between 50° C. and 350° C.

In a fourth embodiment of the composite system of the invention, the second component is embodied as an at least sectionally straight, circularly cylindrical tube, and an inner diameter of a tube stock serving as the second component is equal, i.e. essentially unchanged, at least in the area of the joining surfaces, practically continuously, to an initial, beginning inner diameter of the tube serving as the second component, so that the second component, at least in the area of the joining surfaces, shows essentially no cross sectional tapering and/or narrowing.

In a fifth embodiment of the composite system of the invention, the inner surface of the first component is formed by an inner wall of a bore extending at least in a portion of the first component.

In a sixth embodiment of the composite system of the invention, the outer surface of the second component is formed by an outer wall of the second component.

In a seventh embodiment of the composite system of the invention, at least one of the components, especially both components, is/are subjected to lastingly elastic, especially mixed plastic-elastic, deformations.

In an eighth embodiment of the composite system of the invention, clamping forces, especially normal forces directed radially to the longitudinal axis, act on joining surfaces of the composite system formed by the mutually contacting surfaces of the two components, such that at least one of the two components of the composite system is deformed at least partly lastingly elastically, especially mixed elastically-plastically.

In a ninth embodiment of the composite system of the invention, the contour portions exhibit, at least in part, plastic deformations.

In a tenth embodiment of the composite system of the invention, the contour portions forming the mechanical interference interlocking are at least partly formed by at least partly plastic, especially mixed elastic-plastic, deformation of at least one of the two components, especially directly during the joining of the two components together and/or at a working temperature lying below a recrystallization temperature of the material.

In an eleventh embodiment of the composite system of the invention, the contour portions forming mechanical interference locking are formed, at least in part, by cold forming of at least one of the two components.

In a twelfth embodiment of the composite system of the invention, the two components form, at least in part, a pressed connection effective especially in the direction of the longitudinal axis and/or in a peripheral direction of the outer surface of the second component.

In a thirteenth embodiment of the composite system of the invention, at least two engaged sides of the contour portions overlap one another sufficiently that the mechanical interference locking exhibits a load-bearing depth of at least 0.05 mm, especially greater than 0.1 mm.

In a fourteenth embodiment of the composite system of the invention, the plastic deformation of at least one of the components extends from the associated surface forming the corresponding joining surface with a depth of penetration of at least 0.05 mm, especially greater than 0.1 mm.

In a fifteenth embodiment of the composite system of the invention, engaged sides of the contour portions forming the mechanical interference locking are so inclined relative to the direction of the longitudinal axis, that the mechanical interference locking exhibits a pitch angle of less than 30°, especially less than 10°.

In a sixteenth embodiment of the composite system of the invention, the contour portions forming the mechanical interference locking are formed, at least in part, by machining a surface of at least one of the two components, especially by the cutting of notches, furrows or grooves circularly or helically, especially by the cutting of at least one thread.

In a seventeenth embodiment of the composite system of the invention, at least one side of the contour portions forming the mechanical interference locking is formed, at least in part, by at least one thread, which is situated in at least one of the surfaces of the first or second component forming joining surfaces of the composite system.

In an eighteenth embodiment of the composite system of the invention, the at least one side of the contour portions forming the mechanical interference locking is formed, at least in part, by at least one inner thread situated in a bore of the first component.

In a nineteenth embodiment of the composite system of the invention, the at least one side of the contour portions forming the mechanical interference locking is formed, at least in part, by at least one outer thread situated on an outer periphery of the second component.

In a twentieth embodiment of the composite system of the invention, at least one first side of the contour portions forming the mechanical interference locking is formed, at least in part, by at least one inner thread situated in a bore of the first component and at least one second side of the contour portions forming the mechanical interference locking, especially a second side engaged with the first side, is formed, at least in part, by at least one outer thread situated on an outer periphery of the second component.

In a twenty-first embodiment of the composite system of the invention, the sides of the at least one thread forming the contour portions are at least partially plastically deformed.

In a twenty-second embodiment of the composite system of the invention, the inner thread situated in the first component has a thread pitch which is about equal to a thread pitch of the outer thread on the second component.

In a twenty-third embodiment of the composite system of the invention, the inner thread situated in the first component has a pitch, which is different from a pitch of the outer thread located on the second component.

In a twenty-fourth embodiment of the composite system of the invention, the sides of the inner thread situated in the first component have a side angle, which is about equal to a side angle of the outer thread situated on the second component.

In a twenty-fifth embodiment of the composite system of the invention, the sides of the inner thread situated in the first component have a side angle, which is different from a side angle of the outer thread situated on the second component.

In a twenty-sixth embodiment of the composite system of the invention, for increasing a tensile strength, especially a pull-out resistance of the second component out of the first component in the direction of the longitudinal axis, a thin intermediate layer of an, especially deformable and/or adhesively acting, filler material, especially a plastic, paper, hemp or the like, is arranged between the inner surface of the first component and the outer surface of the second component.

In a twenty-seventh embodiment of the composite system of the invention, a synthetic material, especially an epoxy resin, a fluorine-containing plastic, an elastomer or the like, serves as the filler material.

In a twenty-eighth embodiment of the composite system of the invention, an adhesive, especially an adhesive adhesively bonding to metal, serves as the filler material.

In a twenty-ninth embodiment of the composite system of the invention, a solder, especially a hard-solder, or braze, especially such in the form of a spreadable solder paste applied on at least one of the surfaces forming the joining surfaces or as solder foil laid on one of the surfaces forming the joining surfaces, serves as the filler material.

In a thirtieth embodiment of the composite system of the invention, the solder serving as the filler material is formed by means of a solder foil composed at least partially of an amorphous metal.

In a further development of the composite system of the invention, such further includes a third component, especially one spaced from the first component, with the second component at least partially extending through the third component, wherein the second component so contacts an inner surface of the third component likewise flushly, that the first component at least sectionally grips around the second component, and wherein the joining surfaces of the composite system formed by the mutually contacting surfaces of the second and third components are likewise formed in such a manner that the second and third components exhibit contour portions in the area of these joining surfaces, and these contour portions at least partially interlock to form a mechanical interference locking effective at least in part likewise in the direction of the longitudinal axis.

In an embodiment of this further development of the invention, the second component contacts the inner surface of the third component flushly, such that also the second and third components are partially mechanically tightly connected together by means of frictional locking achieved especially by cold forming of at least one of the two components and effective at least in part in the direction of the longitudinal axis.

In a thirty-first embodiment of the composite system of the invention, one of the components, especially the first component, is made of a first material and at least one other of the components, especially the second component, is made of a second material, with the first material essentially differing from the second material as regards at least one physical and/or chemical property, especially a surface hardness, a yield strength or an offset yield strength, a coefficient of thermal expansion and/or as regards the modulus of elasticity, etc.

In a thirty-second embodiment of the composite system of the invention, the first material has an offset yield strength which is greater than an offset yield strength of the second material.

In a thirty-third embodiment of the composite system of the invention, the first material has an offset yield strength which is smaller than an offset yield strength of the second material.

In a thirty-fourth embodiment of the composite system of the invention, the first material has a yield strength which is greater than a yield strength of the second material.

In a thirty-fifth embodiment of the composite system of the invention, the first material has a yield strength which is smaller than a yield strength of the second material.

In a thirty-sixth embodiment of the composite system of the invention, the first material has a surface hardness which is greater than a surface hardness of the second material.

In a thirty-seventh embodiment of the composite system of the invention, the first material has a surface hardness which is smaller than a surface hardness of the second material.

In a thirty-eighth embodiment of the composite system of the invention, the first material has a modulus of elasticity which is greater than a modulus of elasticity of the second material.

In a thirty-ninth embodiment of the composite system of the invention, the first material has a modulus of elasticity which is smaller than a modulus of elasticity of the second material.

In a fortieth embodiment of the composite system of the invention, the first material has a coefficient of thermal expansion which is greater than a coefficient of thermal expansion of the second material.

In a forty-first embodiment of the composite system of the invention, the first material has a coefficient of thermal expansion which is smaller than a coefficient of thermal expansion of the second material.

In a forty-second embodiment of the composite system of the invention, at least one of the components is made of an essentially ductile material, especially a metal.

In a forty-third embodiment of the composite system of the invention, at least the first component and the second component are each made of metal.

In a forty-fourth embodiment of the composite system of the invention, at least one of the components is made of steel, especially high-grade steel.

In a forty-fifth embodiment of the composite system of the invention, at least one of the components is made of titanium, especially a titanium alloy.

In a forty-sixth embodiment of the composite system of the invention, at least one of the components is made of tantalum, especially a tantalum alloy.

In a forty-seventh embodiment of the composite system of the invention, at least one of the components is made of zirconium, especially a zirconium alloy.

In a forty-eighth embodiment of the composite system of the invention, at least one of the components has a ring-shape.

In a forty-ninth embodiment of the composite system of the invention, at least one of the components is sleeve-shaped.

In a fiftieth embodiment of the composite system of the invention, at least one of the components is tubular.

In a first embodiment of the measurement pickup of the invention, the second component is in the form of a measuring tube serving to convey the medium to be measured, vibrating during operating of the measurement pickup, especially executing, at least at times, bending oscillations about an oscillation axis extending in the direction of the longitudinal axis of the composite system or coinciding with the longitudinal axis of the composite system.

In a second embodiment of the measurement pickup of the invention, the first component is in the form of an, especially plate- or funnel-shaped, end-piece of a support element of the measurement pickup affixed on an end of the measuring tube.

In a third embodiment of the measurement pickup of the invention, the support element is in the form of a pickup housing of the measurement pickup surrounding the measuring tube.

In a fourth embodiment of the measurement pickup of the invention, the support element is in the form of a counteroscillator of the measurement pickup surrounding the measuring tube, especially a cylindrical counteroscillator, extending essentially coaxially with the measuring tube.

In a fifth embodiment of the measurement pickup of the invention, the first component is in the form of a flange of the measurement pickup, affixed on an end of the measuring tube and serving for the connection of a line, in the form of a pipeline, to the measuring tube.

In a sixth embodiment of the measurement pickup of the invention, the contour portions are so arranged and so formed, that the mechanical interference locking counteracts a potentially possible pull-out motion of the measuring tube, at least when the vibrating measuring tube is strained during operation. Especially, the contour portions are so arranged and so formed, that the mechanical interference locking counteracts a potentially possible, or at least virtually present, pull-out motion of the measuring tube also when the vibrating measuring tube is allowed to relax during operation.

In a first embodiment of the method of the invention, the inner surface of the first component and the outer surface of the second component are so formed and the deforming forces acting on the two components are so developed, that the first joining surface of the composite system formed by the inner surface of the first component and the second joining surface of the composite system formed by the outer surface of the second component contact one another lastingly, at least sectionally, accompanied by the formation of a frictional locking likewise effective at least partly in the direction of the longitudinal axis.

In a second embodiment of the method of the invention, the deforming forces are so developed that at least one of the two components is deformed at least partially plastically.

In a third embodiment of the method of the invention, contour portions are formed in the surface of the first component forming the first joining surface of the composite system, as well as in the surface of the second component forming the second joining surface of the composite system, and the contour portions are caused to fit at least partially into one another to form the mechanical interference locking.

In a fourth embodiment of the method of the invention, the contour portions are formed before the step of assembling the first component at least partially with the second component by forming, especially cutting, in at least one of the surfaces of the components a groove or furrow extending essentially circularly or helically in a peripheral direction of the surface.

In a fifth embodiment of the method of the invention, the contour portions are at least partially formed before the assembly of the first component with the second component by situating, especially by cutting, at least one thread in at least one of the surfaces forming the joining surfaces of the composite system.

In a sixth embodiment of the method of the invention, before the assembly of the first component with the second component, at least a first side of the contour portions forming the mechanical interference locking is formed at least in part by at least one inner thread situated in the bore of the first component and at least a second side of the contour portions forming the mechanical interference locking is formed at least in part by at least one outer thread situated on an outer periphery of the second component.

In a seventh embodiment of the method of the invention, the step of assembling the first component with the second component includes a step of screwing the second component into the first component.

In an eighth embodiment of the method of the invention, for forming the joining surfaces of the composite system, the sides of the at least one thread serving as contour portions are at least partially plastically deformed.

In a ninth embodiment of the method of the invention, the contour portions are formed, especially directly during the forming of the joining surfaces of the composite system, at least partially by at least partly plastic deformation of at least one of the components.

In a tenth embodiment of the method of the invention, the contour portions are at least partly formed by plastically deforming at least one of the components, starting with the associated surface forming the relevant joining surface, with a penetration depth, which extends into the material of the at least one component at least 0.05 mm, especially more than 0.1 mm.

In an eleventh embodiment of the method of the invention, the deforming forces serving for forming the joining surfaces of the composite system are produced at least in part by means of a rolling tool, which is placed in a lumen formed in the interior of the second component and surrounded by its outer wall and which is pressed from within, against the outer wall.

In a twelfth embodiment of the method of the invention, the deforming forces serving for forming the joining surfaces of the composite system are produced at least in part by means of a pressing tool, which at least partially grasps the first component and compresses the first component from the outside.

In a first further development of the method of the invention, the method further includes a step of introducing a fluid, especially a liquid or a liquid-gas mixture, into a lumen formed in an interior of the second component.

In an embodiment of this first further development of the method of the invention, the deforming forces serving for the forming of the joining surfaces of the composite system is produced, at least in part, by loading the fluid introduced into the lumen of the second component with a force increasing a static pressure of the fluid.

In a thirteenth embodiment of the method of the invention, the deforming forces serving for forming the joining surfaces of the joining system are produced, at least in part, by heating the first component and thus thermally straining it and/or cooling the second component and thus thermally shrinking it, and by bringing the two components to an essentially equal temperature following the assembly.

In a second further development of the method of the invention, the method further includes a step of applying a filler material, especially a solder or an adhesive, on at least one of the surfaces forming the joining surfaces of the composite system.

In an embodiment of this second further development of the method of the invention, the joining surfaces of the composite system holding the first and second components together at least partly enter into the formation of a bond with the filler material arranged between the first and second components.

In a fourteenth embodiment of the method of the invention, the second component is in the form of an at least sectionally straight, circularly cylindrical tube, and the deforming forces are so developed that the second component experiences, at least in the area of the joining surfaces, essentially no cross sectional tapering and/or narrowing and that an initial inner diameter of the second component is maintained practically unchanged throughout, at least in the area of the joining surfaces, even after the step of the forming of the joining surfaces of the composite system holding the first and the second components together.

A basic idea of the invention is to affix separate components of a vibration-type measurement pickup, for example the affixing of the measuring tube in the outer support element and/or in the counteroscillator, at least partly by means of a mechanical interference locking provided in the area of the joining surfaces usually directly contacting one another.

It has been found to be especially advantageous here to implement this affixing of the separate components both, in part, by means of a frictionally locking connection and, in part, by means of a mechanical interference locking connection, placed especially in the area of the frictionally locking connection or integrated therein, or, stated differently, to construct the measurement pickup at least partially by means of such composite systems, so that its components are connected together by a mixture of mechanical interference locking and frictional locking. Moreover, by the partially plastic, especially the mixed elastic-plastic, deformation of individual surfaces and/or contour portions or also entire components, it is especially possible to produce the mechanical interference locking very accurately in simple manner and, at the same time, to achieve extremely good load-bearing ability.

A further advantage of the invention is, among other things, that, in case required, a soldering, brazing or welding process for the affixing of the measuring tube in the measurement pickup can be avoided, since, already by the mixing of mechanical interference locking and frictional locking, a very stable, high-strength and lasting, mechanical connection between the components of the composite system can be achieved, especially also in spite of continuing vibrational loading of the composite system. Corresponding investigations have, for example, shown that, while avoiding supplemental solder, braze or weld connections, alone composite systems of the described kind formed by frictional locking permit direct achievement of pull-out strength increased by a factor of three. A further advantage of the invention is that the cold-forming, affixing methods already described in U.S. Pat. No.-A 5,610,342 or U.S. Pat. No.-A 6,047,457 and subsequently proved in practice can be applied, and, correspondingly, also the already installed press and/or rolling equipment can predominantly continue to be used. Additionally, with use of the aforementioned press or rolling equipment, it becomes, on the one hand, possible, alone by the continued use of machine and tool settings recognized as optimum for the manufacture of conventional composite systems, to achieve a marked improvement of the pull-out strength and, therefore, also of the longterm endurance. Now, on the other hand, in comparison to conventional composite systems with composite systems formed with purely frictionally locked connections, it is also considerably easier to assure that the measuring tube, despite the high clamping forces with which it is held in the support element, itself scarcely experiences any deformation, and, consequently, even after installation, a largely constant, uniform cross section is maintained over the entire length of the measuring tube.

As a further advantage, especially compared to conventional composite systems formed in part or entirely by means of bonding, must be mentioned the considerable simplification of manufacture and also the lowering of manufacturing costs. Moreover, the required high quality of the composite system, be it with respect to the material properties of the used components or be it with respect to mechanical strength, can not only be increased but, also, be reproduced far more reliably.

BRIEF DESCRIPTION OF THE DRAWINGS

The invention, as well as advantageous embodiments, will now be explained in greater detail on the basis of the drawing, the figures of which show as follows.

DETAILED DESCRIPTION OF EXEMPLARY EMBODIMENTS

Figure 1:
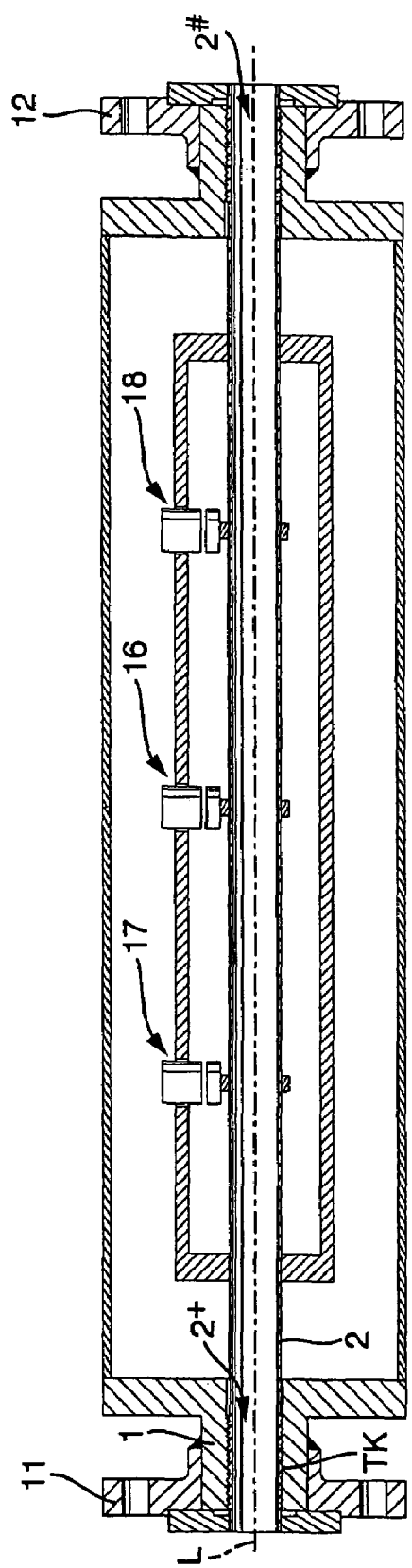
FIG. 1 partially in section, a longitudinal view of a vibration-type measurement pickup, especially in the form of a Coriolis mass flow rate pickup, having at least two components combined as a composite system.

While the invention is susceptible to various modifications and alternative forms, exemplary embodiments thereof have been shown by way of example in the drawings and will herein be described in detail. It should be understood, however, that there is no intent to limit the invention to the particular forms diclosed, but on the contrary, the intention is to cover all modifications, equivalents, and alternatives falling within the spirit and scope of the invention as defined by the intended claims.

Figure 2:
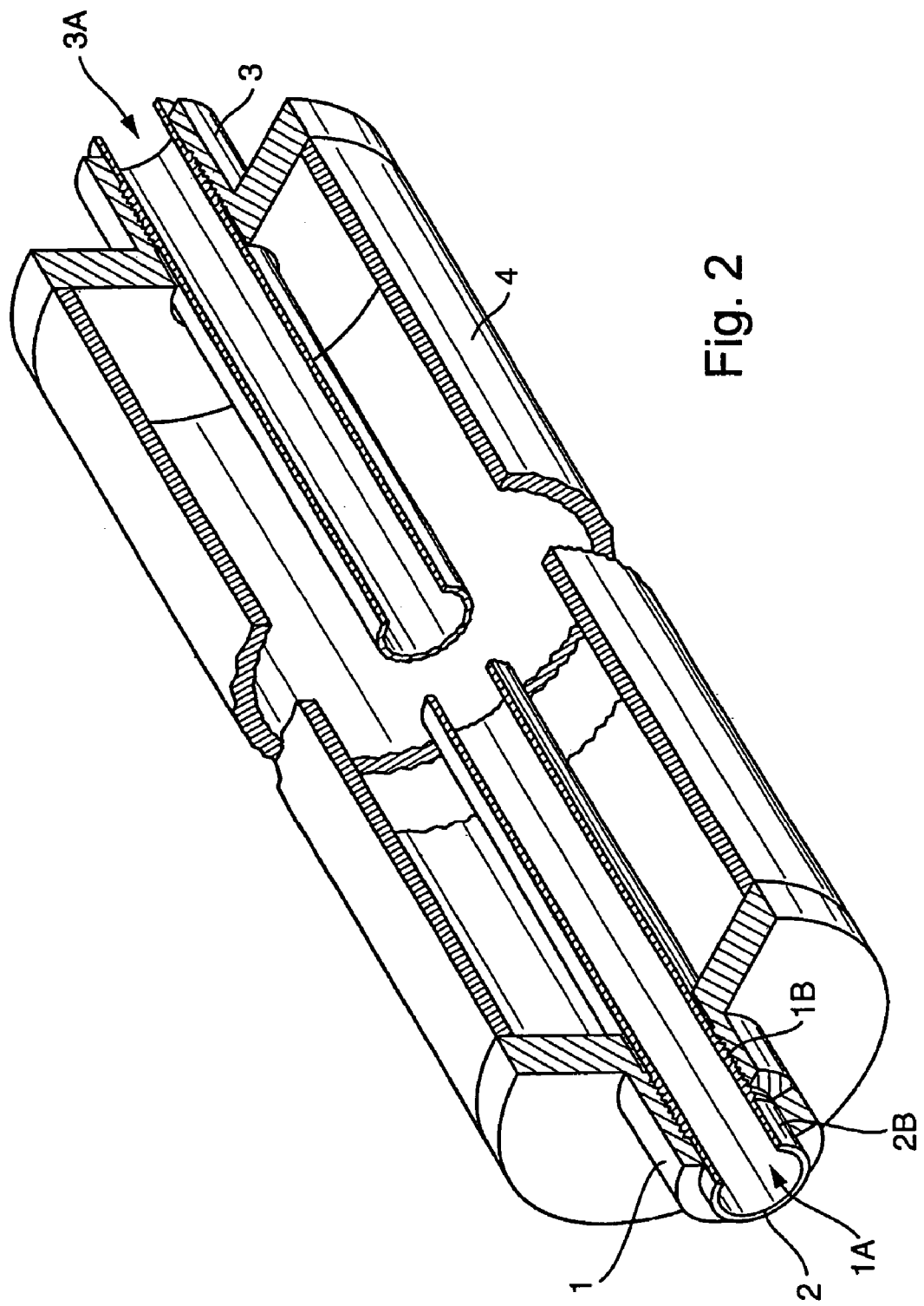
FIG. 2 perspectively, in partly sectional view, a composite system suited for use in a measurement pickup according to FIG. 1, with at least a first and a second component.

FIG. 1 shows an example of an embodiment for an, especially bi-metal, composite system formed of a first component 1 and a second component 2 extending at least partially through the first component along an imaginary longitudinal axis L of the composite system. As can be seen in FIG. 2, the second component 2 has, in such case, an at least partially curved, outer surface, especially a cylindrical outer surface, which so contacts an inner surface of the first component flushly, that the first component grasps the second component at least sectionally, at least partly, whereby first and second joining surfaces 1B, 2B of the composite system are created. For increasing the longterm strength of the composite system, especially for increasing the pull-out strength of its second component 2 out of the first component 1, the joining surfaces 1B, 2B of the composite system formed by the, especially directly, contacting surfaces of the two components are formed such that the two components 1, 2 have in the region of these joining surfaces, especially in the form of self-closing, peripheral surfaces, contour portions TK, which at least partially fit into one another to form a mechanical interference locking effective, at least in part, likewise in the direction of the longitudinal axis L.

In an embodiment of the invention, at least one of the components of the composite system has, in such case, additionally lasting plastic deformations in the area of the joining surfaces, with these extending into the material from the associated surface forming the corresponding joining surface, preferably with a depth of penetration of at least 0.05 mm, especially, however, of greater than 0.1 mm. To this end, in an embodiment of the method of the invention, contour portions TK are formed into the surface of the first component 1 forming the first joining surface 1B of the composite system and into the surface of the second component 2 forming the second joining surface 2B of the composite system, and the contour portions TK are, as also shown schematically in FIGS. 3 to 6 or photographically in FIG. 7, brought following the assembly of the two components at least partially to fit into one another to form the mechanical interference locking. Alternatively thereto or in supplementation thereof, the two components, together with their mutually contacting surfaces, are, in a further embodiment of the invention further so developed and formed that the two components 1, 2, as also schematically shown in FIG. 2, are mechanically connected tightly together partly by the formation of a frictional locking effective at least partly in the direction of the longitudinal axis. Preferably, the surfaces of the components 1, 2 are further so formed that the frictional locking produced thereby also acts in a peripheral direction of the outer surface of the second component 2. This is accomplished in this embodiment of the composite system of the invention by allowing clamping forces, especially normal forces F directed radially to the longitudinal axis L, to act such that at least one of the two components of the composite system is at least partially, lastingly elastically deformed. These normal forces are produced, at least in part, in an embodiment of the invention by providing that at least one of the two components 1, 2 is deformed mixed elastically-plastically, thus exhibiting both plastically deformed regions, which have been introduced therein by straining or compression of the involved component, and also elastically deformed regions resulting therefrom. The two components 1, 2 of the composite system thus form, at least in part, a pressed joint effective especially in the direction of the longitudinal axis L and/or in a peripheral direction of the outer surface of the second component 2. The materials used for the components 1, 2 can be, for example, materials essentially equal to one another, or at least similar. However, the composite system of the invention can also, without difficulty, lastingly and safely join components, which significantly differ from one another as regards at least one physical and/or chemical property, for example as regards their coefficients of thermal expansion, their elastic moduli, their surface hardnesses, their offset yield strengths and/or their yield strengths, their recrystallization temperatures, their melting temperatures, etc. For example, the material of the first component 1 can have an elastic modulus, which is greater than an elastic modulus of the material of the second material and/or a coefficient of thermal expansion, which is greater than a coefficient of thermal expansion of the material of the second component 2 and/or a surface hardness, which is greater than a surface hardness of the material of the second component 2 and/or a yield strength or offset yield strength, which is greater than a yield strength or offset yield strength of the material of the second component 2, etc., or vice versa.

Due to its lastingly very high mechanical strength, especially also in the presence of forces alternating at mid- or high-frequency, the composite system of the invention is very well suited for use in vibration-type measurement pickups. The example of an embodiment shown in FIG. 1 is, consequently, a composite system, which is formed of individual components of a vibration-type measurement pickup, e.g. a Coriolis mass flow rate measurement pickup illustrated in sectioned, longitudinal view. In use, such pickup is inserted in a pipeline (not shown) and connected thereto fluid-tightly, before start-up. However, only the essentials of such measurement pickup needed for the explanation of the invention are shown in FIG. 1; the remaining, and, for complete functioning of the measurement pickup, necessary components are not shown, in order to focus attention on the essentials for this invention. This is possible, especially, because the construction, function and areas of application are, per se, known to those skilled in the art; the documents of the state of the art already mentioned above are incorporated by reference as regards such omitted structure.

In the case of the composite system shown, by way of example, in FIG. 1, the first component is embodied as a first endpiece having a bore 1A provided therein, which accommodates an inlet-end, straight, essentially circularly cylindrical, first tube segment of a—here only partially shown—measuring tube of the measurement pickup, so that this functions to such extent as a second component 2 of the composite system. In the case of the shown example of an embodiment, thus the inner surface of the first component 1 serving as first joining surface 1B of the composite system is formed by an inner wall of the bore 1A extending completely through the first endpiece, while the outer surface 2B of the second component 2 serving as second joining surface 2B of the composite system is formed by an outer wall of the measuring tube. As additionally observable from FIG. 1, a second tube segment of the measuring tube, especially one of essentially identical form as the first tube segment, is inserted into a bore 3A of a second endpiece of the measurement pickup, especially an end piece of essentially identical form to that of the first end piece. In an embodiment of the invention, the second tube segment and the second endpiece are connected together in the same manner as the first tube segment and the first endpiece 11. The first endpiece and the second endpiece (functioning, for practical purposes, as third component 3 of the composite system) are, furthermore, completed by means of at least one, laterally arranged, mounted or welded, support plate or an essentially cylindrical support tube 4 to form a support element oscillatably holding the at least one measuring tube.

The second component 2 in the form of a measuring tube in the example of an embodiment shown here is provided to be inserted into the course of a pipeline flowed-through by a fluid to be measured, e.g. a liquid or a gas, and to be so connected fluid-conductively therewith, that the fluid to be measured can also flow through the measuring tube during operation of the corresponding measurement pickup. To this end, appropriate flanges 11, 12 are provided, which are connected via respective, short tubular pieces, with the respective end pieces, into which inlet end 2+ and outlet end 2# of the single measuring tube shown here opens. Instead of via the flanges, the measurement pickup can also be connected to the pipeline by means of other, usual securement means, for example by means of so-called TriClamp® connectors or also by means of screwed connections.

For producing reaction forces corresponding with a physical, measured variable, e.g. a mass flow rate, a density and/or a viscosity of the fluid and thus describing the fluid, e.g. reaction forces such as Coriolis forces correlated with the mass flow rate or frictional forces correlated with the viscosity, etc., the measuring tube—driven by an electromechanical, oscillation exciter interacting therewith—is caused to vibrate, at least at times during operation, with the two tube segments being subjected to axially oscillating, strain-related forces at least partially in the direction of an oscillation axis essentially coinciding with the mentioned longitudinal axis of the composite system imaginarily connecting the two tube segments. Thus, the vibrating measuring tube executes, at least virtually during operation, the kind of pull-out motion potentially lastingly decreasing the pull-out strength. The oscillation exciter 16 can be one of the different kinds of oscillation exciters described for this purpose in the state of the art of such vibration-type measurement pickups, especially those used as Coriolis mass flow rate measurement pickups. By means of the oscillation exciter 16, the measuring tube 13 is excited during operation to bending oscillations, whose oscillation frequency is usually equal to an instantaneous, mechanical eigenfrequency of the measuring tube with fluid conveyed therein.

For the registering of vibrations of the measuring tube and for producing vibration signals corresponding to these, appropriate oscillation sensors can be placed in the vicinity of the measuring tube in manner (not detailed here) known to those skilled in the art. For instance, FIG. 1 shows first and second sensors 17, 18 provided, respectively, for the movements of the measuring tube on the inlet and outlet ends; these sensors are arranged at about equal distances between the halfway point of the measuring tube and the respective inlet and outlet end pieces. In the example of an embodiment shown in FIG. 1, approximately circular ring- or circular washer-shaped metal bodies are, furthermore, located on the measuring tube at the locations of the respective sensors. These metal bodies interact with the sensors 17, 18 and are shown again, this time enlarged, in FIG. 8 in a perspective side view. Sensors 17, 18 can, for such purpose, be any of the various types of sensors described in the state of the art as used for such vibration-type measurement pickups, especially Coriolis mass flow pickups, sensors such as e.g. electrodynamic or optically working, distance, velocity or acceleration sensors.

It is still to be mentioned at this location, that, instead of the first component 1 embodied in the example as an endpiece and, as far as the region of the, especially frictionally bound together, joining surfaces is concerned, more sleeve shaped first component, it is also possible to use tubular or, as also shown in FIG. 1, more ring-shaped or also washer-shaped metal bodies as the first component 1. Besides the examples of embodiments shown here for the first component 1, having essentially circularly-shaped outer contours, further also such components can be used, which have a non-circular outer contour, for example in the nature of a hexagonal nut, a square disk or also in the manner shown in U.S. Pat. No.-A 6,047,457 with a lateral projection, etc. To this end, one embodiment of the invention provides a component 1 in the form of a metal body, which has a bore matched to an outer peripheral surface 2A of the second component 2 embodied as measuring tube, which has a corresponding inner peripheral surface, and which has been appropriately affixed on the outer peripheral surface 2A of the measuring tube to form the composite system. The component 1 embodied in FIG. 1 as ring- or washer-shaped, metal bodies can, as already indicated, serve as holders for the already mentioned oscillation sensors or the oscillation exciter or, however, also, as proposed in WO-A 03/027616, as stiffening elements stabilizing the cross section of the measuring tube also in the case of pressure fluctuations.

As can be recognized without difficulty from the above explanations, the present invention is concerned with maximizing a pull-out strength of the composite system and, along with that, also a long-term strength of the composite system. For the described case, in which the components 1, 2, 3 of the composite system are components of a vibration-type measurement pickup, of concern also, besides the maximizing of the pull-out strength of the composite system, is especially the increasing of a vibration, or fatigue, strength and, therefore, of a maximum possible or allowable number of cycles to failure for the measuring tube. Accordingly, the contour portions TK for this case are arranged and formed, as much as possible, such that the mechanical interference locking at least then counteracts a potentially possible or at least virtually present pull-out movement of the measuring tube, when the vibrating measuring tube undergoes strain during operation. Advantageously, the contour portions TK are furthermore arranged and formed as much as possible, such that the mechanical interference locking also then counteracts a potentially possible or at least virtually present pull-out motion of the measuring tube, when the vibration measuring tube is allowed to relax during operation.

Figure 3:
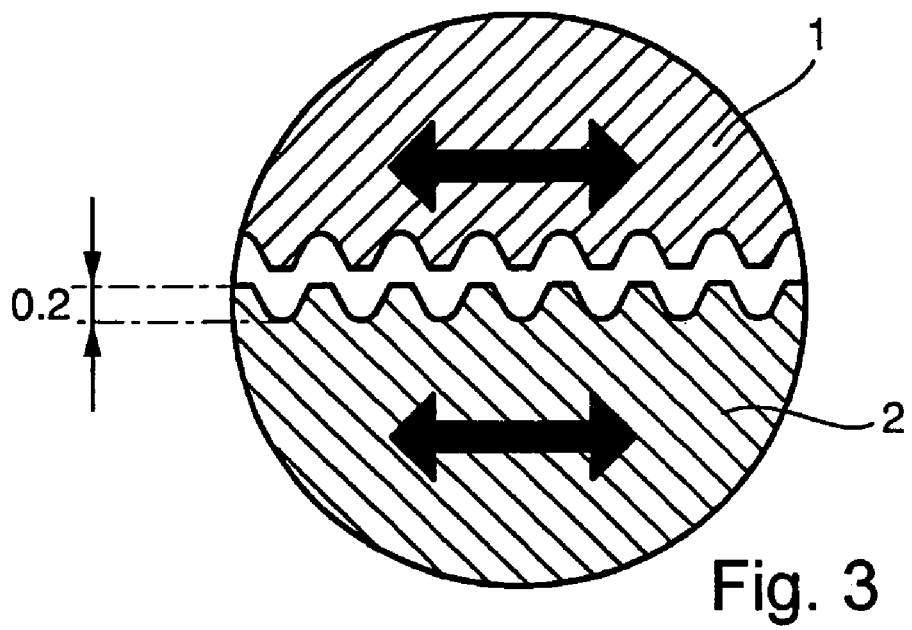
FIG. 3 enlarged view, in each case in longitudinal section, of segments of the first and second components of FIG. 2 bearing contour portions for a mechanical interference locking, immediately before assembly of the two components.
Figure 4:
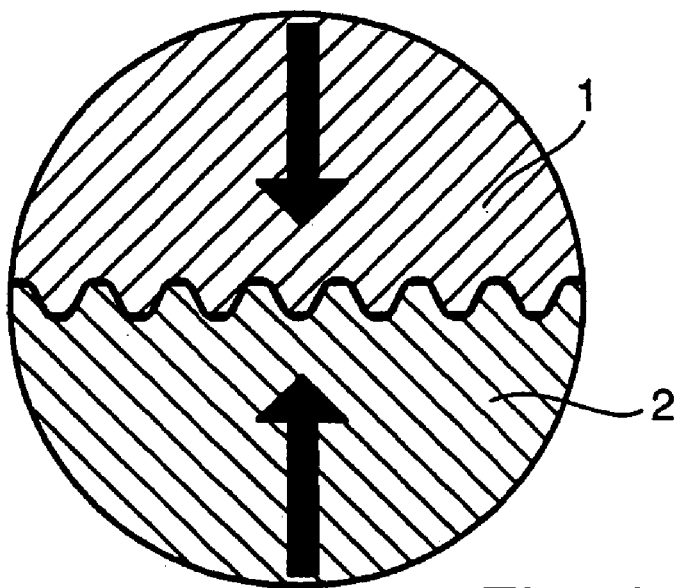
FIGS. 4 to 6 enlarged views, in each case in longitudinal section, of different embodiments of segments of the first and second components of FIG. 2 with mechanical interference locking, following assembly of the two components.

For manufacturing the composite system, the first component 1—thus, for example, the aforementioned endpiece—is, as illustrated schematically in FIG. 3, assembled with the second component 2—thus, for example, the measuring tube—in a manner such that the second component 2 extends in the direction of the longitudinal axis L of the composite system at least partially through the bore 1A formed in the first component 1. Then, the joining surfaces 1B, 2B of the composite system joining the two components 1, 2 are formed, as schematically illustrated in FIG. 4, by allowing the deformation forces F to act on at least one of the two components in such a way that at least one of the two components 1, 2 is deformed at least in part elastically, especially mixed elastically-plastically, thus both partly plastically and partly elastically. In an embodiment of the method of the invention, the inner surface of the first component 1 and the outer surface of the second component 2 are so formed therefor and the deforming forces F acting on the two components 1, 2 are so developed, that a first joining surface 1B of the composite system formed by the inner surface of the first component 1, especially in the form of a self-closing peripheral surface, and a second joining surface 2B of the composite system formed by the outer surface of the second component 2, especially in the form of a self-closing, peripheral surface, lastingly contact one another, at least sectionally, even after the manufacturing process, accompanied by the formation of a frictional locking effective at least partly in the direction of the longitudinal axis L, as well as by the formation likewise of a mechanical interference locking effective at least partly in the direction of the longitudinal axis. This is achieved in an embodiment of the method of the invention by deforming at least one of the two components 1, 2 at least partially plastically, such that lasting mechanical stresses are built-up therein and, therefore, at least in this component, especially, however, in both components 1, 2, lastingly elastic deformations arise; compare, in this connection, especially also the initially mentioned U.S. Pat. No.-A 5,610,342, U.S. Pat. No.-A 6,047,457 or U.S. Pat. No.-B 6,519,828. To this end, at least one of the components 1, 2, in a further development of the invention, is made of an essentially ductile, thus plastically deformable, material. For example, the material of the components 1, 2 of the composite system can be a metal, for example a high-grade, stainless, steel, titanium, tantalum, zirconium or a corresponding alloy thereof.

Figure 7:
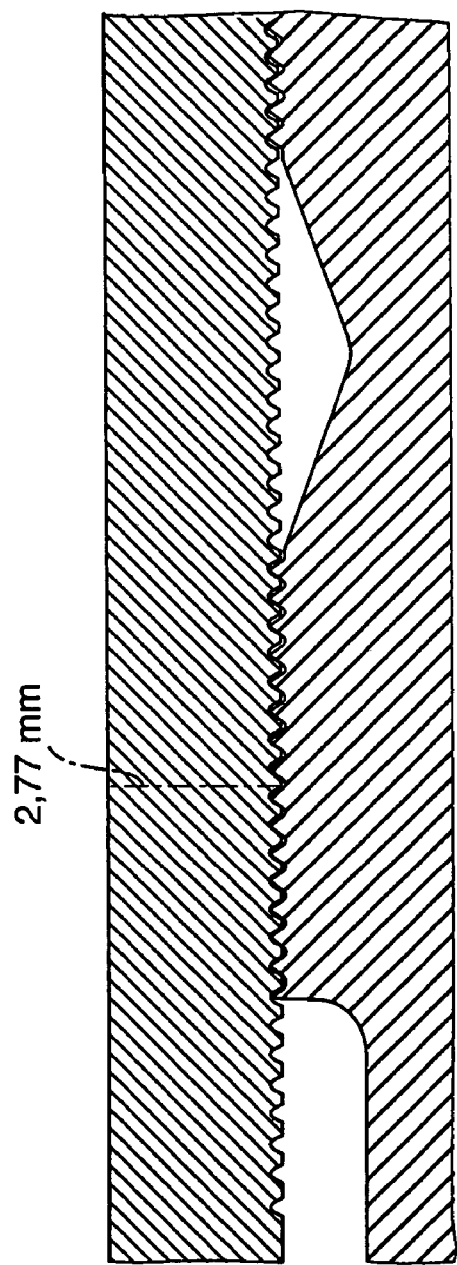
FIG. 7 photographically in longitudinal section, segments of the first and second components of FIG. 2 with mechanical interference locking, following assembly of the two components.

In order to achieve as high an axial pull-out strength as possible in the direction of the longitudinal axis L of the composite system, at least two mutually engaged sides of the contour portions TK forming the mechanical interference locking overlap one another in an embodiment of the invention to such an extent that the mechanical interference locking has a load-bearing depth of at least 0.05 mm, especially greater than 0.1 mm; compare also FIG. 7 in this connection. The contour portions TK forming the mechanical interference locking can, for example, be created beforehand by machining of a surface of at least one of the two components, especially by the cutting of notches, furrows or grooves running circularly or helically about the longitudinal axis L, or, however, also by plastic deformation of at least one of the surfaces forming the joining surfaces, e.g. by rolling and/or pressing.

In a further embodiment of the invention, engaged sides of the contour portions TK forming the mechanical interference locking are at least partly so inclined with respect to the direction of the longitudinal axis, that the mechanical interference locking exhibits a pitch angle of less than 30°, especially less than 10°. Based on the parameters usual for the dimensioning of screw threads, "pitch angle" means an angle which a tangent applied to each side makes, measured from a reference axis directed perpendicularly to the longitudinal axis L.

In another embodiment of the invention, to this end, at least one side of the contour portion TK forming the mechanical interference locking is formed, at least in part, by at least one thread, which is situated in at least one of the surfaces of the first or second component forming the joining surfaces 1B, 2B of the composite system. For example, the at least one side of the contour portions TK forming the mechanical interference locking can be formed, at least in part, by at least one internal thread situated in the bore 1A of the first component 1 or, at least in part, by at least one external thread situated on the outer periphery of the second component 2.

In a further development of this embodiment of the invention, however, both at least a first side of the contour portions TK forming the mechanical interference locking is formed, at least in part, by at least one internal thread situated in the bore 1A of the first component 1, as well as also at least a second side of the contour portions TK forming the mechanical interference locking, especially a second side engaged with the first side, is formed, at least in part, by at least one external thread situated on an outer periphery of the second component. To this end, in a further development of the method of the invention, the contour portions TK are formed before the step of assembling the first component with the second component 2, at least partially, by forming into at least one of the surfaces of the components at least one groove or one furrow, which runs essentially circularly or helically in a peripheral direction of the surface. In an embodiment of this further development of the method, the contour portions TK are accordingly formed at least partially before the step of assembling the first component 1 with the second component 2 by situating at least one thread in at least one of the surfaces forming the joining surfaces 1B, 2B of the composite system, by cutting or rolling such into the surface.

Figure 5:
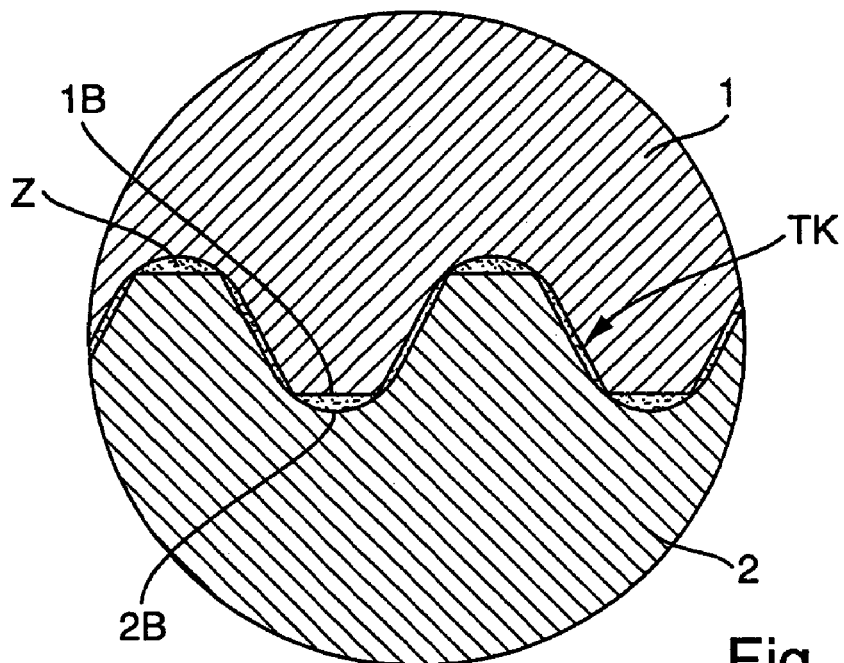
Figure 6:
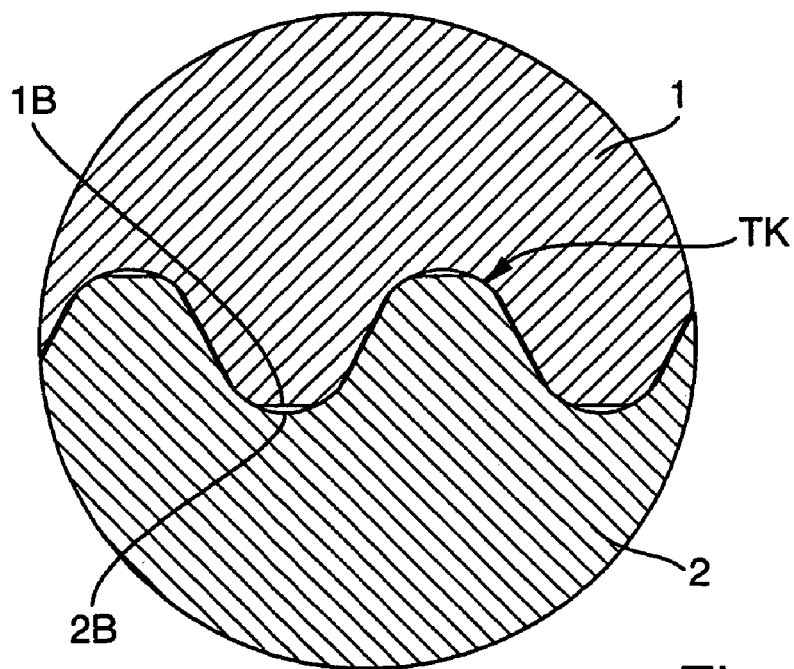

In a further embodiment of the invention, the outer thread and internal thread are so situated that the first and second components are screwed together by means of the two threads. In this way, the assembly of the first component 1 with the second component 2 can occur in simple manner, wherein the second component 2 is correspondingly screwed into the first component 1, whereby the two components are practically automatically oriented with respect to one another and with reference to the longitudinal axis of the composite system. To this end, the inner thread situated in the first component 1 has, in a further development of this embodiment of the invention, a thread pitch, which is about equal to a thread pitch of the external thread situated on the second component 2. In another, further development of this embodiment of the invention, the internal thread situated in the first component has, however, a thread pitch, which is different from a thread pitch of the external thread situated in the second component. In another embodiment of this further development of the invention, the sides of the internal thread situated in the first component has a thread side angle, which is different from a thread side angle of the external thread situated on the second component. For example, in the case of one of the two threads, such can be a sharp thread, while the other thread is in the form of a flat thread. Alternatively, the internal and external threads can, however, also be embodied, such that the thread side angle of the internal thread situated in the first component can, as also indicated in FIG. 5, be about equal to the thread side angle of the external thread situated on the second component. As indicated in FIG. 5, the contour portions TK, for example the sides forming the contour portions TK of the at least one thread, exhibit in a further embodiment of the invention plastic deformations, at least in part, whereby there is provided some axial, as well as radial, play between the two components, especially in order to accommodate material-related, differing thermal expansions of the two components due to temperature fluctuations within the composite system.

It is to be noted here that, instead of a thread, or in supplementation thereof, the contour portions for the mechanical interference locking can, however, also be formed by notches, grooves or furrows worked into the surfaces forming the joining surfaces. These notches, grooves or furrows can be distributed in the direction of the longitudinal axis of the composite system and run on peripheral, for instance circumferential, lines of the joining surface of interest, for example as complete, self-closing annular grooves or as open, annular grooves extending at least partially around. Additionally, the contour portions can have, instead of the somewhat trapezoidal cross sections of FIGS. 3, 4, 5 or 6, also other suitable cross sectional forms, such as e.g. a triangularly shaped cross section.

In another embodiment of the method of the invention, the contour portions are formed partially by at least partially plastic deformation of at least one of the components directly during the assembly of the two components 1, 2 and the associated forming of the joining surfaces of the composite system. This can be done in simple manner e.g. by first appropriately situating the above-mentioned internal thread or the above-mentioned external thread in the described manner before the assembly of the components 1, 2 and the sides of the thread are then pressed into the corresponding surface of the complementary component 1 or 2 during the assembling of the components. In a further development of this embodiment of the invention, the contour portions are formed by plastically deforming at least one of the components 1, 2,—starting from the associated surface forming the corresponding joining surface—with a penetration depth of at least 0.05 mm, especially more than 0.1 mm, into the material of the at least one component.

In a further development of the invention, for further increasing the pull-out strength of the second component out of the first component in the direction of the longitudinal axis and/or for improving the fluid-tightness of the composite system, a thin, intermediate layer of an, especially deformable and/or adhesively acting, filler material Z is arranged between the inner surface of the first component and the outer surface of the second component. For the case in which the filler material is to be applied in liquid and/or pasty condition onto the surfaces or distributed on the surfaces, the filler material Z can be appropriately liquified by mixing with suitable softeners and/or by warming. In an advantageous embodiment of this further development, the filler material is so constituted, that the joining surfaces 1B, 2B of the composite system joining the first and second components together at least partially bond with the filler material Z between the first and second components 1, 2. The filler material can be, for example, a synthetic material, or plastic, such as an epoxide resin, a fluorine-containing plastic, an elastomer or the like, and/or an adhesive, especially one adhesively bonding to metal. Furthermore, an, especially suitably coated, weave and/or paper or hemp can serve as the filler material. In another embodiment of this further development of the invention, a solder, especially a hard-solder, or braze, can serve as filler material, e.g. in the form of a spreadable solder-paste, applied to at least one of the surfaces forming the joining surfaces, especially one melting below a recrystallization temperature of at least one of the materials used for the components 1, 2. For example, also a solder can be used for this, which is composed at least in part of an amorphous metal and which is, for example, in the form of a solder foil, which is laid before or during assembly of the two components 1, 2 onto at least one of their surfaces forming the joining surfaces.

In another further development of the invention, the frictional locking is formed, at least in part, by plastic, especially mixed elastic-plastic, deformation of at least one of the two components at a working temperature below a recrystallization temperature of the material, especially also below the recrystallization temperature of the material of the first component and below the recrystallization temperature of the material of the second component, wherein the recrystallization temperature can be considered, in the broadest sense, that temperature, at which mechanical stresses accumulated in the material of the particular component is essentially erased again by a new arrangement of the metal grains. Stated differently, this embodiment of the invention permits forming of the contour portions creating the mechanical interference locking at least in part by cold forming of at least one of the two components. For example, the forming can occur at a working temperature of less than 350° C. However, it can be of advantage, especially when using filler material Z laid between the components, to use a working temperature for the forming that is, at least at times, in a temperature range above 15° C., especially at room temperature or above. In an advantageous embodiment of this aforementioned further development of the invention, the contour portions TK forming the mechanical interference locking are at least partially produced by at least partially plastic, especially mixed elastic-plastic, deformation of at least one of the two components. This can occur e.g. directly during the assembly of the two components 1, 2 and, consequently, if necessary, also at a working temperature lying below a recrystallization temperature of the material. For example, a part of the contour portions can be situated before the assembly of the two components in at last one of the surfaces later forming the joining surfaces, for example by forming either the mentioned internal thread in the first component or the mentioned external thread in the second component and directly during assembly be allowed to act on the other, complementary surface in such a manner that the still missing, complementary part of the contour portions is formed by pressing of the earlier, already formed, contour portions into the complementary surface. For the above-mentioned case in which the material of the first component has a surface hardness differing from the surface hardness of the material of the second component, the earlier formed contour portions should be situated in the component whose material has the greater of the two surface hardnesses, in order that a mechanical interference locking can be achieved having the greatest possible load-bearing depth.

Figure 9:
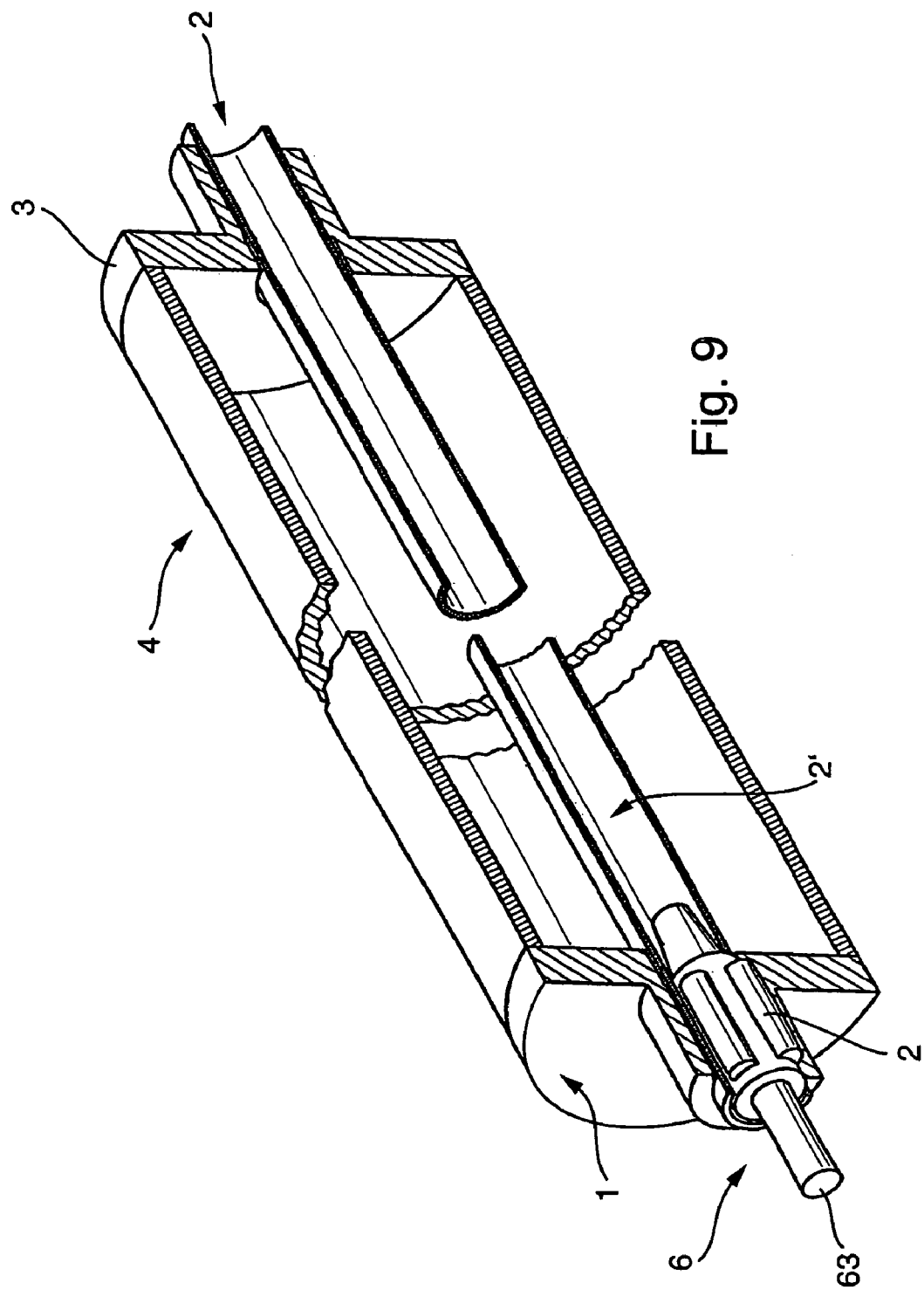
FIG. 9 perspectively, a method step of a corresponding manufacturing method for the composite system of FIG. 2, for the affixing of the second component in the first component.

The deformation forces F required for the lasting deformation, especially also for the cold-forming, of the at least one component and, associated therewith, for the forming of the joining surfaces 1B, 2B of the composite system can, for example, and as also proposed in U.S. Pat. No.-A 5,610,342 or WO-A 03/048693, be produced, at least in part, by means of a rolling tool 6, which is, as illustrated in FIG. 9, placed in a lumen 2' formed in the interior of the second component and surrounded by its outer wall and pressed from the inside against the outer wall. On the front end in the insertion direction, the rolling tool 6 carries a cage 61 having rollers 61 distributed on its cylindrical, lateral surface and set in corresponding openings. The circle along which the rollers 62 move during rotation of the rolling tool 6 has a radius which can be adjusted by means of a member 63 that is movable in the direction of insertion. By increasing this radius as compared with the radius with which the rolling tool 6 is first inserted into the lumina of the measuring tubes 1, 2, the tool can be pressed sectionally against the inner wall of the second component 2. The tube segment is thus pressed in this way, especially without supply of heat, against the inner wall of the bore 1A in the first component 1. By this, a slight flow of the material of the second component 2 occurs and, in this way, at these locations, especially also in the area of the contour portions TK, a very strong, mechanical connection is achieved between the components 1, 2. The pressure produced by means of the rolling tool, as well as form and size of the contour portions, are, in such case, to be matched to one another such that, in the region of the contour portions TK, or in the region provided in total for the joining surfaces 1B, 2B, a sufficient amount of material of the second component 2 is caused to flow. Due to the aforementioned plastic deformation of the second component 2 in the form of a tube segment, there is, in part, a small lessening of its wall thickness and, consequently, on the one hand, a mechanical compressive stress in the longitudinal axis of the second component, since this is slightly lengthened. On the other hand, also a mechanical compressive stress arises within the first component 1 in the radial direction; this is referred to as "radial stress" in the following. The radial stress can be attributed to the fact that, during the pressing, it is true that the second component is partially plastically deformed, while, in contrast, the first component 1 is essentially only elastically deformed, because of its much greater thickness compared to the wall thickness of the second component 2, so that, consequently, after the pressing, the first component 1 exerts a normal force in the form, under the circumstances, of a radial force directed toward the lumen of the second component onto the joining surfaces.

Figure 8:
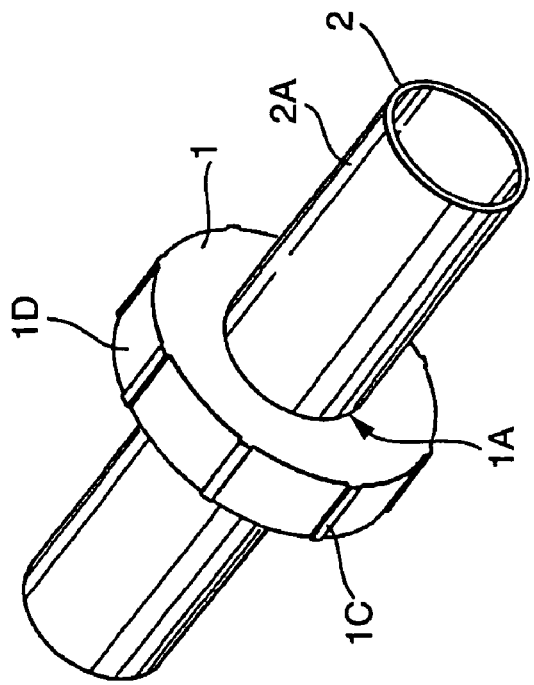
FIG. 8 perspectively, a circular, washer-shaped, metal body, serving as first component of the composite system of FIG. 2, on an only partially shown, circularly cylindrical measuring tube of a vibration-type measurement pickup serving as second component of the composite system of FIG. 2.

Alternatively or in supplementation thereto, the deforming forces required for the lasting deformation of at least one of the components can at least partially be produced, for example, by, as also described in U.S. Pat. No.-A 6,047,547, compressing the first component mechanically externally by a pressing tool at least partially grasping the component, such that the component is at least partially deformed plastically. In such case, an essentially radially inwardly acting pressure sufficient for the affixing of the components together is exerted by means of the pressing tool on at least a portion of an outer peripheral surface of the first component by two or more cheeks of the pressing tool contacting the peripheral surface flushly. In the affixed state, a peripheral surface of the first component 1 then may show, as also indicated in FIG. 8, depression surfaces 1D at the locations where contact was made by the cheeks of the pressing tool, which depression surfaces lie slightly deeper than the adjoining portions 1C of the peripheral surface, where the pressure was not applied. This is an indication that plastic deformation has occurred in the region of the peripheral surface. In such case, these plastic deformations are formed such that they, in turn, deform the first and the second components at least partially, lastingly elastically, as much as possible, and, consequently, permanently produce clamping forces acting in the radially inwards direction, as normal forces F, on the joining surfaces 1B, 2B in sufficient measure for the affixing.

For the above-described case in which the second component is to serve as measuring tube and, to such end, is formed as an at least sectionally straight, circularly cylindrical tube, preferably, however, only a pressure is exerted on the first component, such that the lumen of the second component in the form of a tube is essentially not narrowed at the location of affixing. Accordingly, the deformation forces are thus developed in an advantageous embodiment of the invention such that the second component, at least in the region of the joining surfaces, essentially experiences no cross sectional tapering and/or narrowing and that an initial inner diameter of the second component remains essentially continuous and essentially unchanged at least in the region of the joining surfaces after the step of forming the joining surfaces of the composite system binding the first and second components together. To this extent, it can be assured, without more, that, for example, the second component 2, in the form of a measuring tube, itself scarcely experiences any deformations, despite the high clamping forces, with which it is held in the first component 1 in the form of a support element, and, consequently, also after installation, there is a largely constant, uniform cross section over the entire length of the measuring tube.

Alternatively or in supplementation of the aforementioned pressing method or the aforementioned rolling method, the deformation forces required for the deformation can also be at least partly produced, for example, hydraulically, in that a suitable fluid, especially a liquid such as oil or water or a liquid-gas mixture is introduced into a lumen formed in the inside of the second component, for example, thus, the lumen of the measuring tube and in that this fluid introduced into the lumen of the second component is loaded with a force increasing a static pressure of the fluid. Additionally, the deformation forces required for the deformation of the at least one component and thus also serving for the formation of the joining surfaces of the composite system can also be produced, at least in part, by, as indicated also in U.S. Pat. No.-B 6,598,281 or U.S. Pat. No.-B 6,519,828, heating the first component 1 and, consequently, thermally expanding it and/or by cooling the second component 2 and, consequently, thermally shrinking such, and by then bringing the two components to an essentially equal temperature after the assembly.

As will be evident without difficulty from the totality of the above explanations, an advantage of the invention lies, in particular, also in the fact that the composite system, or the method for its manufacture, is especially also suited for application to components composed of different materials, where, thus, the utilized materials significantly differ from one another with respect to at least one physical and/or chemical property, for example with regards to their coefficients of thermal expansion, their moduli of elasticity, their surface hardnesses, their offset yield strengths and/or their yield strengths, their recrystallization temperatures, their melting temperatures, etc. For the case where the materials used for the components of the composite system of the invention are metals, these can, moreover, without more, differ, as regards material, from one another in a manner such that they are not, or only with significant effort as regards manufacturing technology, weldable with one another. Accordingly, in a further embodiment of the invention, the first component is a steel or high grade steel or stainless steel, while the material for the second component is titanium, zirconium, tantalum or a metal alloy of at least one of the aforementioned, high corrosion resistance metals. For example, the materials used for the components 1, 2 can each be a steel-type differing from the other. A further advantage of the invention is that the composite system is suited, as, for example evident from FIG. 2, especially also for the joining of a massive and relatively rigid component, such as e.g. the endpiece 1, with an, in comparison, easily deformable, relatively thin-walled component, such as the measuring tube. Moreover, the pull-out strength of the composite system of the invention, even after multiple-oscillation loading, can, without more, be above 50% of the originally present, relatively high, initial pull-out strengths and, consequently, can be maintained, without more, even for a long duration of operation, still above the minimum strengths required for measurement pickups of the described kind.

With knowledge of the invention and with the background of the initially referenced state of the art, especially U.S. Pat. No.-A 5,610,342, U.S. Pat. No.-A 6,047,457, U.S. Pat. No.-A 6,168,069, U.S. Pat. No.-B 6,519,828, U.S. Pat. No.-B 6,598,281 or WO-A 03/048693, there is also no difficulty for those skilled in the art to determine suitable materials for the components for a particular application, as well as optimum parameters, be it with regard to the actual dimensioning of the components of the composite system or with regard to the adjustment of the tools and machines used for the manufacturing. Equally, there is also no difficulty for those skilled in the art to adapt the method of the invention as regards the specific requirements for durability of the composite system and to optimize such as regards the manufacturing process therefor.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A vibration-type measurement pickup for a measuring device serving to measure a medium flowing in a line, said measurement pickup comprising a composite system defining a imaginary longitudinal axis, and including:
   a first component; and
   a second component, said second component extending at least partly through said first component along said imaginary longitudinal axis, such that said first component at least sectionally, at least partly, grips around said second component, and said second component contacting, with an outer surface thereof, an inner surface of said first component by formation of a frictional interlocking effective at least partly in the direction of said imaginary longitudinal axis wherein:
   said first component includes a contour portion formed in the area of said inner surface;
   said second component includes a contour portion formed in the area of said outer surface, said contour portions at least partly fit into one another to provide mechanical interference locking effective at least in part likewise in the direction of said imaginary longitudinal axis.

2. The measurement pickup as claimed in claim 1, wherein:
   the frictional interlocking is formed at least partly by plastic deformation of at least one of said first and second components at a working temperature lying below a recrystallization temperature of the material, and/or;
   the frictional interlocking is formed by at least partly plastic, especially mixed elastic-plastic deformation of the at least one of said first and second components at a working temperature held at least at times in a temperature range between 50° C. and 350° C., and/or;
   at least one of said first and second components is subjected at least partly to lastingly elastic or mixed plastic-elastic deformations.

3. The measurement pickup as claimed in claim 1, wherein:
at least one of said first and second components is subjected, at least partly, to mixed plastic-elastic deformations.

4. The measurement pickup as claimed in claim 1, wherein:
the inner surface of said first component is formed by an inner wall of a bore extending at least in a portion of said first component.

5. The measurement pickup as claimed 1, wherein:
the outer surface of said second component is formed by an outer wall of said second component.

6. The measurement pickup as claimed in claim 1, wherein:
clamping forces, especially normal forces directed radially to said imaginary longitudinal axis act on said inner surface of said first component and on said outer surface of said second component, such that at least one of said first and second components is deformed at least partly lastingly elastically or mixed elastically-plastically.

7. The measurement pickup as claimed in claim 1, wherein:
the contour portions exhibit, at least in part, plastic deformations.

8. The measurement pickup as claimed in claim 1, wherein:
the contour portions forming the mechanical interference locking are at least partly formed by at least partly plastic or mixed elastic-plastic deformation of at least one of said first and second components accomplished especially directly during the assembly of said first and second components together and/or at a working temperature lying below a recrystallization temperature of the material.

9. The measurement pickup as claimed in claim 1, wherein:
said first and second components form, at least in part, a pressed connection effective especially in the direction of said imaginary longitudinal axis and/or in a peripheral direction of the outer surface of said second component.

10. The measurement pickup as claimed in claim 1, wherein:
at least two engaged sides of the contour portions overlap one another sufficiently that the mechanical interference locking exhibits a load-bearing depth of at least 0.05 mm, especially greater than 0.1 mm;
the engaged sides of the contour portions forming the mechanical interference locking exhibits a pitch angle of 30°, and;
the contour portions forming the mechanical interference locking are formed, at least in part, by a machined surface of at least one of said first and second components.

11. The measurement pickup as claimed in claim 1, wherein:
at least one side of the contour portions forming the mechanical interference locking is formed, at least in part, by at least one thread, which is situated in said inner surface of said first component and said outer surface of said second component, respectively.

12. The measurement pickup as claimed in claim 1, wherein:
at least one of the contour portions forming the mechanical interference locking is formed, at least in part, by at least one internal thread situated in a bore of said first component;
one of the contour portions forming the mechanical interference locking is formed, at least in part, by at least one outer thread situated on an outer periphery of said second component; and
at least one first side of the contour portions forming the mechanical interference locking is formed, at least in part, by at least one inner thread situated in a bore of said first component and at least one second side of the contour portion forming the mechanical interference locking, especially a second side engaged with the first side, is formed, at least in part, by at least one outer thread situated on an outer periphery of said second component.

13. The measurement pickup as claimed in claim 11, wherein:
said at least one thread forming the contour portions comprises sides which are at least partially plastically deformed.

14. The measurement pickup as claimed in claim 1, wherein:
for increasing a tensile strength, especially a pull-out resistance of said second component out of said first component in the direction of the imaginary longitudinal axis, a thin intermediate layer of an, especially deformable and/or adhesively acting, filler material, especially plastic, paper, hemp, is arranged between the inner surface of said first component and the outer surface of said second component.

15. The measurement pickup as claimed in claim 1, further including;
a third component, especially one spaced from said first component, with said second component at least partly extending through said third component such that said third component at least sectionally grips around said second component;
said second component contacting, with an outer surface, an inner surface of said third component by formation of a frictional locking effective at least partly in the direction of said imaginary longitudinal axis; and
said third component includes a contour portion formed in the area of said inner surface of said third component, and said second component includes a contour portion being formed in the area of said outer surface contacting said inner surface of said third component and fitting at least partially into said contour portion formed in the area of said inner surface of said third component to provide mechanical interference locking effective at least in part likewise in the direction of said imaginary longitudinal axis.

16. The measurement pickup as claimed in claim 1, wherein:
said first component is made of a first material and said second component is made of a second material, with the first material essentially differing from the second material as regards at least one physical and/or chemical property.

17. The measurement pickup as claimed in claim 1, wherein:
at least one of said first and second components is made of an essentially ductile material.

18. The measurement pickup as claimed in claim 1, wherein:

said first component and said second component are made of metal.

19. The measurement pickup as claimed in claim 1, wherein:
at least one of said first and said second components is made of a metal selected from the group consisting of: steel, high-grade steel, stainless steel, titanium, titanium alloy, tantalum, tantalum alloy, zirconium and zirconium alloy.

20. The measurement pickup as claimed in claim 1, wherein:
at least one of said first and said second components is one of; ring-shaped, sleeve shaped and tubular.

21. The measurement pickup as claimed in claim 1, wherein:
at least one of the contour portions forming the mechanical interference locking is formed, at least in part, by at least one outer thread situated on an outer periphery of said second component.

22. The measurement pickup as claimed in claim 1, wherein:
said second component is in the form of a measuring tube, said measuring tube serving to convey the medium to be measured; and
said measuring tube vibrating during operation of the measurement pickup.

23. The measurement pickup as claimed in claim 22, wherein:
said first component is in the form of an end-piece of a support element of the measurement pickup; and
said end-piece being affixed on an end of the measurement pickup.

24. The measurement pickup as claimed in claim 23, wherein:
said support element is in the form of a pickup housing of the measurement pickup, and
said pickup housing surrounding said measuring tube.

25. The measurement pickup as claimed in claim 23, wherein:
said support element is in the form of a counter oscillator of the measurement pickup; and
said counter oscillator surrounding said measuring tube and extending essentially coaxially with said measuring tube.

26. The measurement pickup as claimed in claim 22, wherein:
said first component is in the form of a flange of the measurement pickup; and
said flange being affixed on an end of said measuring tube and serving for the connection of a line, in the form of a pipeline, to said measuring tube.

27. The measurement pickup as claimed in claim 22, wherein:
the contour portions are so arranged and so formed that the mechanical interference locking counteracts a potentially possible pull-out motion of said measuring tube, at least when said measuring tube is strained during operation of the measurement pickup, and/or;
that the mechanical interference locking counteracts a potentially possible, or at least virtually present, pull-out motion of said measuring tube when said measuring tube is allowed to relax during operation of the measurement pickup.

28. The measurement pickup as claimed in claim 16, wherein:
the at least one physical and/or chemical property, with the first material essentially differing from the second material, is selected from surface hardness, yield strength, offset yield strength, coefficient of thermal expansion, and modulus of elasticity.

29. The measurement pickup as claimed in claim 2, wherein:
the plastic deformation of at least one of said components extends from the associated surface forming the corresponding joining surface with a depth of penetration of at least 0.05 mm.

30. The measurement pickup as claimed in claim 2, wherein:
the plastic deformation of at least one of said components extends from the associated surface forming the corresponding joining surface with a depth of penetration greater than 0.1 mm.

31. The measurement pickup as claimed in claim 1, wherein:
the contour portions forming the mechanical interference locking are formed, at least in part, by at least one of; the cutting of notches, furrows and grooves.

32. The measurement pickup as claimed in claim 1, wherein:
the contour portions forming the mechanical interference locking are formed, at least in part, by cutting of at least one thread.

33. The measurement pickup as claimed in claim 1, wherein:
at least a first one of the contour portions forming the mechanical interference locking is formed, at least in part, by at least one inner thread situated in a bore of said first component, and;
at least a second one of the contour portions forming the mechanical interference locking is formed, at least in part, by at least one outer thread situated on an outer periphery of said second component.

34. The measuring pickup as claimed in claim 33, wherein:
a side of said inner thread is engaged with a side of said outer thread.

35. A method for the manufacture of a measurement pickup of a vibration-type for a measuring device serving to measure a medium flowing in a line, the measurement pickup comprising a composite system including: a first component with an inner surface, which is formed by an inner wall of a bore extending at least into a portion of the first component, and a second component with an outer wall which forms the outer surface of the second component, said method comprising the steps of:
assembling the first component with the second component in a manner such that the second component extends at least partially through the bore formed in the first component in the direction of an imaginary longitudinal axis of the composite system, and
forming joining surfaces of the composite system joining the first and second components together, wherein:
for the forming of the joining surfaces of the composite system, deformation forces are caused to act on at least one of the first and the second components in a manner such that at least one of the first and the second components is deformed at least partially elastically; and
the inner surface of the first component and the outer surface of the second component are so formed and the deformation forces acting on the first component and the second component are so developed, that a first joining surface of the composite system formed by the inner surface of the first component and a second joining surface of the composite system formed by the outer surface of the second component contact one another lastingly at least sectionally on the basis of a mechanical interference locking effective at least in part in the direction of the imaginary longitudinal axis.

36. The method as claimed in claim 35 wherein:
the inner surface of the first component and the outer surface of the second component are so formed and the deformation forces acting on the first and second components are so developed that the first joining surface of the composite system formed by the inner surface of the first component and the second joining surface of the composite system formed by the outer surface of the second component contact one another lastingly, at least sectionally, accompanied by the formation of a frictional locking likewise effective at least partly in the direction of the imaginary longitudinal axis.

37. The method as claimed in claim 36, wherein:
the deformation forces are so developed that at least one of the first component and the second component is deformed at least partially plastically.

38. The method as claimed in claim 36, wherein:
contour portions are formed in the inner surface of the first component forming the first joining surface of the composite system, as well as in the outer surface of the second component forming the second joining surface of the composite system; and
the contour portions are caused to fit at least partially into one another to form the mechanical interference locking.

39. The method as claimed in claim 35, wherein:
the first component includes a contour portion formed in the area of the inner surface, and the second component includes a contour portion formed in the area of said outer surface, the contour portions, at least partially, fit into one another to provide the mechanical interference locking effective at least in part likewise in the direction of the imaginary longitudinal axis; and
the contour portions are formed before the step of assembling the first component at least partially together with the second component by forming in at least one of the surfaces of the components a groove or furrow extending essentially circularly or helically in a peripheral direction of the surface.

40. The method as claimed in claim 39, wherein:
the contour portions are at least partially formed before the step of assembling the first component with the second component by situating, especially by cutting, at least one thread in at least one of the surfaces forming the joining surfaces of the composite system.

41. The method as claimed in claim 40, wherein:
before the step of assembling the first component with the second component, at least a first side of the contour portion forming the mechanical interference locking is formed at least in part by at least one inner thread situated in the bore of the first component and at least a second side of the contour portions forming the mechanical interference locking is formed at least in part by at least one outer thread situated on an outer periphery of the second component.

42. The method as claimed in claim 41, wherein:
the step of assembling the first component with the second component includes a step of screwing the second component into the first component.

43. The method as claimed in claim 40, wherein:
for forming said first and second joining surfaces of the composite system, the sides of the at least one thread are at least partially plastically deformed.

44. The method as claimed in claim 39, wherein:
the contour portions are formed, especially directly during the forming of the first and second joining surfaces of the composite system, at least partially by at least partly plastic deformation of at least one of the components.

45. The method as claimed in claim 44, wherein:
the contour portions are at least partly formed by plastically deforming at least one of the components, starting with the associated surface forming the relevant joining surface, with a penetrating depth, which extends into the material of the at least one component at least 0.05 mm, especially more than 0.1 mm.

46. The method as claimed in claim 36, wherein;
the deformation forces serving for forming the first and second joining surfaces of the composite system are produced at least in part by means of a rolling tool, which is placed in a lumen formed in an interior of the second component and surround by an outer wall of the second component, and which is pressed from within, against the outer wall.

47. The method as claimed in claim 36, further comprising the step of:
introducing a fluid, especially a liquid or a liquid-gas mixture into a lumen formed in an interior of the second component.

48. The method as claimed in claim 47, wherein:
the deformation forces serving for forming of the first and second joining surfaces of the composite system are produced, at least in part, by loading the fluid introduced into the lumen of the second component with a force increasing a static pressure of the fluid.

49. The method as claimed in claim 36, wherein:
the deformation forces serving for forming the first and second joining surfaces of the composite system are produced, at least in part, by heating the first component and thus thermally expanding the first component.

50. The method as claimed in claim 36, further including the step of:
applying a filler material, especially a solder or an adhesive, on at least one of the inner and outer surfaces forming the first and second joining surfaces of the composite system.

51. The method as claimed in claim 50, wherein:
the joining surfaces of the composite system holding the first and second components together, at least partly, enter into the formation of a bond with the filler material arranged between the first and second components.

52. The method as claimed in claim 37, wherein:
the second component is in the form of an at least sectionally straight, circularly cylindrical tube; and
the deformation forces are so developed that the second component experiences, at least in the area of the joining surfaces, essentially no cross sectional tapering and/or narrowing, and that an initial inner diameter of the second component is maintained practically unchanged throughout, at least in the area of the joining surfaces, even after the step of forming of the joining surfaces of the composite system holding the first and the second components together.

53. The method as claimed in claim 35, wherein:
the outer wall of the second component is formed at least sectionally cylindrical.

54. The method as claimed in claim 35, wherein:

the outer surface of the second component is formed cylindrical.

55. The method as claimed in claim 35, wherein:

at least one of the first and second components is deformed at least partially mixed elastically-plastically.

56. The method as claimed in claim 35, wherein:

the inner surface of the first component, which forms the first joining surface of the composite system, is formed as a self-closing peripheral surface, and the outer surface of the second component, which forms the second joining surface of the composite system, is formed as a self-closing peripheral surface.

57. The method as claimed in claim 36, wherein:

the deformation forces serving to form the first and second joining surfaces of the composite system are produced, at least in part, by means of a pressing tool, which grips at least partly around the first component and compresses externally.

58. The method as claimed in claim 36, wherein:

the deformation forces serving to form the first and second joining surfaces of the composite system are produced, at least in part, by cooling the second component and thus thermally shrinking the second component, and by bringing the first and second component to an essentially equal temperature following the assembly.

59. The method as claimed in claim 39, wherein:

the contour portions are formed before the step of assembling the first component, at least partially together with the second component by cutting the groove or furrow in the at least one of the surfaces of the first and second components.

* * * * *